(12) United States Patent
Li et al.

(10) Patent No.: US 7,109,380 B2
(45) Date of Patent: Sep. 19, 2006

(54) CYCLOPENTENEDIONE ANTIFUNGAL COMPOUNDS AND METHODS FOR THEIR USE

(75) Inventors: Xing-Cong Li, Oxford, MS (US); Melissa R. Jacob, Oxford, MS (US); David Wedge, Oxford, MS (US)

(73) Assignees: The University of Mississippi, University, MS (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/093,695

(22) Filed: Mar. 29, 2005

(65) Prior Publication Data

US 2005/0215648 A1    Sep. 29, 2005

Related U.S. Application Data

(60) Provisional application No. 60/557,323, filed on Mar. 29, 2004.

(51) Int. Cl.
C07C 49/00 (2006.01)
A61K 31/12 (2006.01)

(52) U.S. Cl. ............... 568/379; 514/684; 514/687

(58) Field of Classification Search ............ None
See application file for complete search history.

(56) References Cited

U.S. PATENT DOCUMENTS 3,852,470 A   12/1974  Grohe et al. ............. 424/331
6,844,353 B1   1/2005  Wedge et al. ............ 514/280

FOREIGN PATENT DOCUMENTS

| DE | 2140737 | 2/1973 |
| DE | 2248819 | 4/1974 |
| DE | 2804271 | 8/1998 |
| JP | 51019125 | 2/1976 |
| JP | 52079022 | 7/1977 |
| JP | 53101336 | 9/1978 |
| WO | WO99/04777 | 2/1999 |

OTHER PUBLICATIONS

Kiang, H. H.; Sim, K. Y. J. Chem. Soc. 1962, 4338.
Lee, H. H. Tetrahedron Lett. 1968, 4243.
Liu, S. Y.; Ogihara, Y. Yakugaku Zasshi 1975, 95, 114.
Leong, et al., J. D. Phytochemistry 1998, 47, 891.
Aoyama, et al.; Bioorg. Med. Chem. Lett. 2001, 11, 1695.
Inayama, S.; Mamoto, K.; Shibata, T.; Hirose, T. J. Med. Chem. 1976, 19, 433.
Shestak, P.; Novikov, V. L.; Stekhova, S. I.; Gorshkova, I. A. Pharm. Chem. J. 1999, 33, 18.
Hori, H.; Nagasawa, H.; Ishibashi, M.; Uto, Y.; Hirata, A.; Saijo, K.; Ohkura, K.; Kirk, K. L.; Uehara, Y. Bioorg. Med. Chem. 2002, 10, 3257.
Watanabe, M.; Hisamatsu, S.; Hotokezaka, H.; Furukawa, S. Chem. Pharm. Bull. 1986, 34, 2810.
Kalinin, A. V.; Snieckus, V. Tetrahedron Lett. 1998, 39, 4999.
Bruce, J. M.; Creed, D.; Dawes, K. J. Chem. Soc. (C) 1971, 3749.
Irngartinger, H.; Stadler, B. Eur. J. Org. Chem. 1998, 605.
Brehm, I.; Meier, H. Eur. J. Org. Chem. 2001, 3307.
Brehm, I.; Hinneschiedt, S.; Meier, H. Eur. J. Org. Chem. 2002, 3162.
Forsén, S.; Merényi, F.; Nilsson, M. Acta Chem. Scand. 1964, 18, 1208.
Ng, S.; Lee, H.-H.; Bennett, G. J. Magn. Reson. Chem. 1990, 28, 337.
Ferreira, D.; Roux, D. G. J. Chem, Soc. Perkin Trans I 1977, 134.
Clemo, N. G.; Gedge, D. R.; Pattenden, G. J. Chem. Soc., Perkin Trans. 1 1981, 1448.
Li, X.-C.; ElSohly, H. N.; Nimrod, A. C.; Clark, A. M. J. Nat. Prod. 1999, 62, 767.
Marr, K. A., Lyons; C. N, Rustad, T; Bowden, R. A, White, T. C. Antimicrob. Agents Chemother. 1998, 42, 2584.
White T. C. Antimicrob. Agents Chemother. 1997, 41, 1482.
Pfaller, M. A.; Rhine-Chalberg, J.; Redding, S. W.; Smith, J.; Farinacci, G.; Fothergill, A. W.; Rinaldi, M. G. J. Clin. Micro. 1994, 32, 59.
Odds, F. C. Int. J. Std. AIDS 1992, 3, 157.
Coleman, D. C.; Bennett, D. E.; Sullivan, D. J.; Gallagher, P. J.; Henman, M. C.; Shanley, D. B.; Russell, R. J. Crit. Rev. Microbiol. 1993, 19, 61.
Nilsson, M. Acta Chem. Scand. 1964, 18:441.
Novikov, V. L.; Shestak, O. P.; Kamernitskii, A. V.; Elyakov, G. B. Izvestiya Akademii Nauk SSR, Seriya Khimicheskaya 1981, 1, 236.
Choi, Y. H.; Kwon, S. Y.; Kim, J. H.; Beak, N. I.; Choi, G. J.; Cho, K. Y.; Lee, B. M. Han'guk Nonghua Hakhoechi 2003, 46:151.
NCCLS, Reference Method for Broth Dilution Antifungal Susceptibility Testing of Yeasts; Approved Standard M27-A2. National Committee on Clinical Laboratory Standards, 2002 22 (15).

(Continued)

*Primary Examiner*—Johann Richter
*Assistant Examiner*—Sikarl A. Witherspoon
(74) *Attorney, Agent, or Firm*—Stites & Harbison PLLC; Richard S. Myers, Jr.

(57) ABSTRACT

Compounds and methods useful in the control, treatment, and prevention of fungal activity, of the following formula:

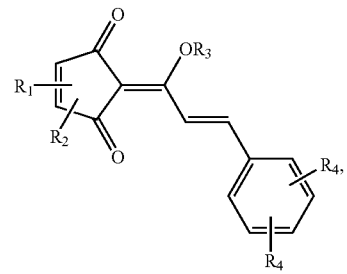

where $R_{1-3}$ are independently H, alkyl, methyl, acyl, halogen, phenyl, $R_4$ is H, alkyl, methyl, acyl, alkoxy, halogen, phenyl provided that when $R_3$ is methyl and $R_4$ is H, $R_1$ and $R_2$ are not both H; and stereoisomers, analogs, and pharmaceutically acceptable salts thereof.

22 Claims, 8 Drawing Sheets

OTHER PUBLICATIONS

NCCLS, Reference method for broth dilution antifungal susceptibility testing of filamentous fungi; approved standard, M38-A. National Committee on Clinical Laboratory Standards, 2002, 22(16).

NCCLS, Methods for Dilution Antimicrobial Susceptibility Tests for Bacteria that Grow Aerobically M7-A5. National Committee on Clinical Laboratory Standards, 2000, 20(2).

NCCLS, Susceptibility Testing of Mycobacteria, Nocardia, and Other Aerobic Actinomycetes; Tentative Standard—Second Edition, M24-T2. National Committee on Clinical Laboratory Standards, 2000, 20(26).

Franzblau, S.G.; Witzig, Richard S.; Mclaughlin, James C.; Torres, Patricia; Madico, Guillermo; Hernandez, Antonio; Degnan, Michelle T.; Cook, Mary B.; Quenzer, Virginia K.; Ferguson, Robert M.; Gilman, Robert H. J. Clin. Microbiol.1998, 36, 362.

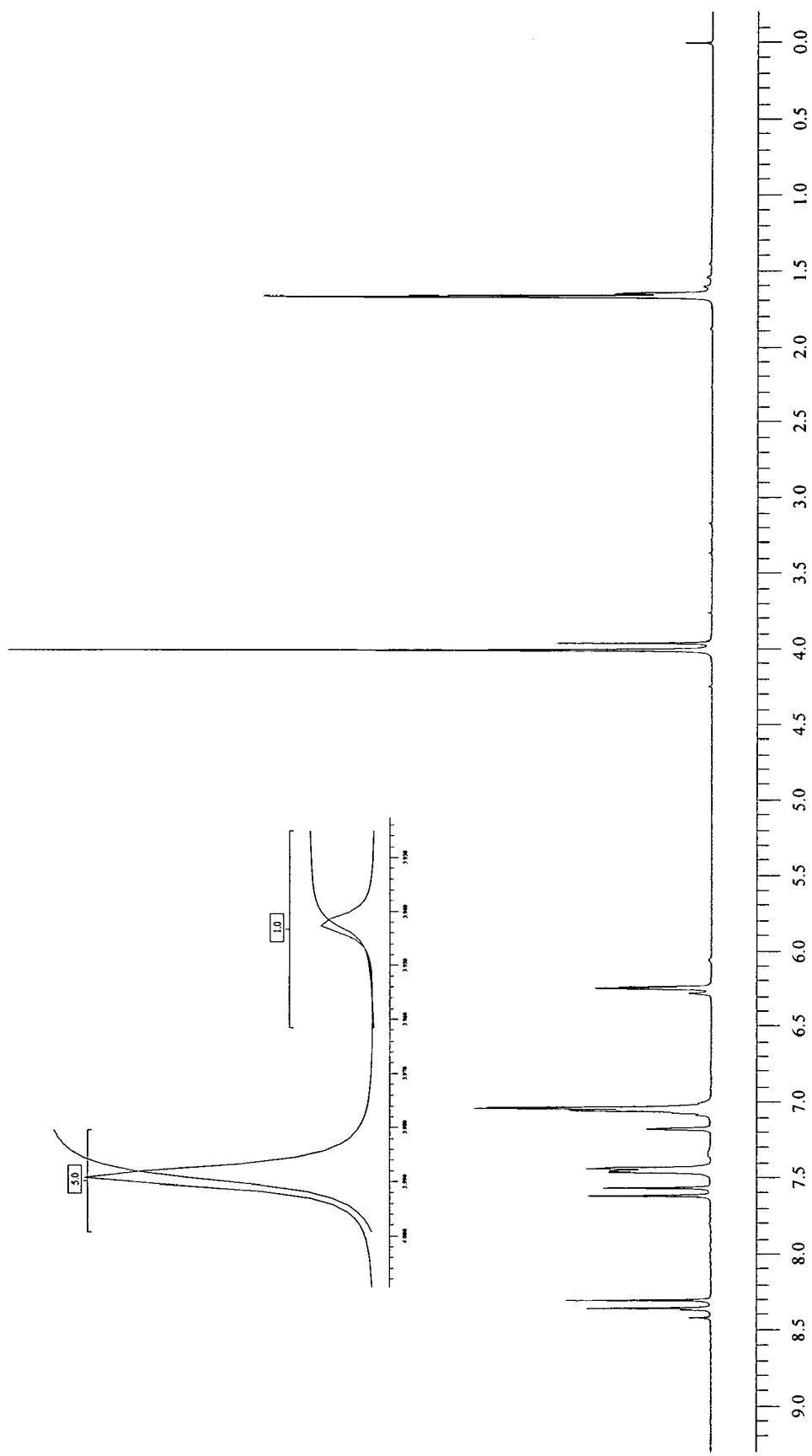
*Figure 1. 300 MHz $^1$H NMR spectrum of coruscanone A (1) in $C_6D_6$ (1a/1b: ~5/1).*

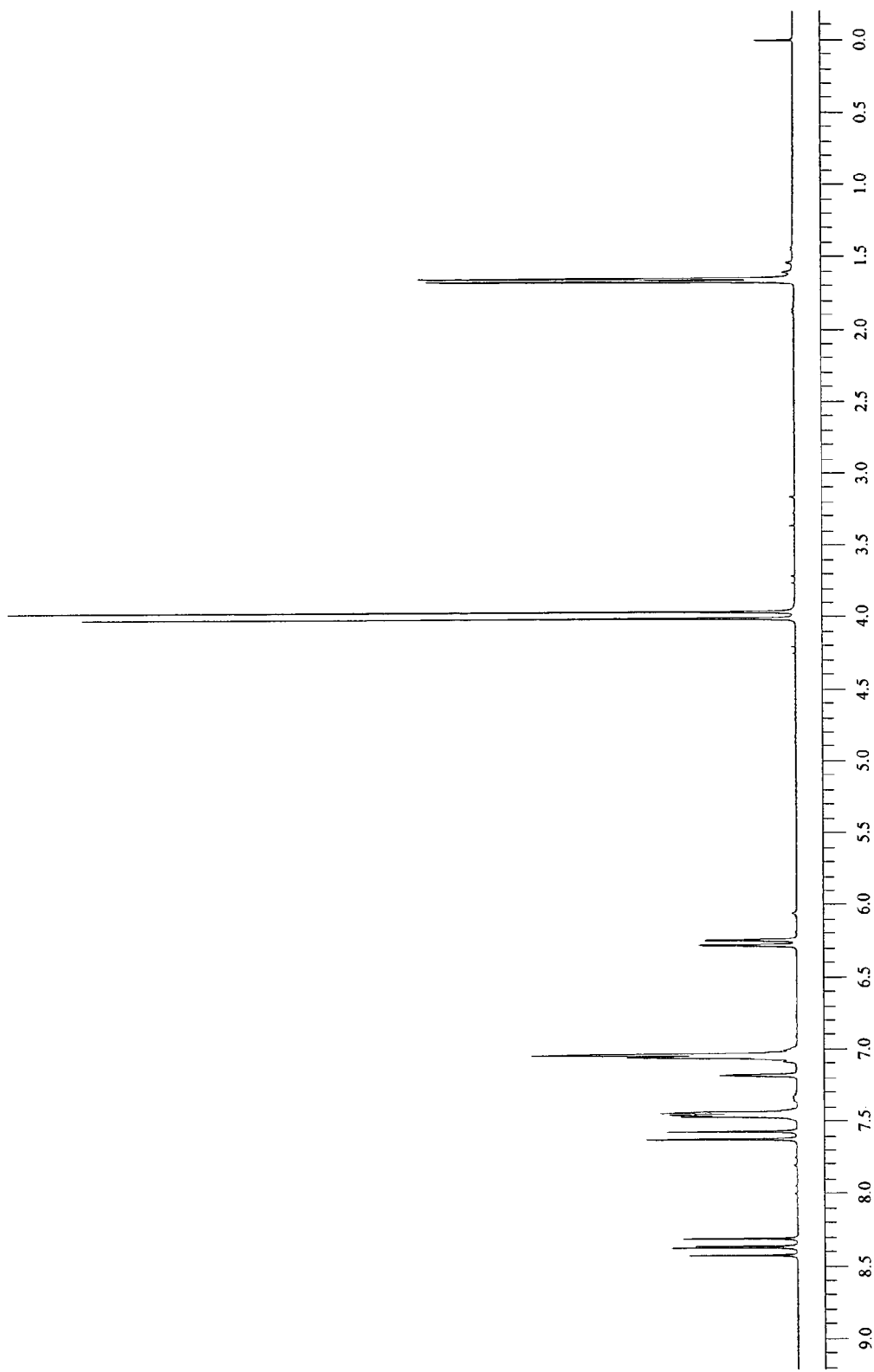
*Figure 2.* 300 MHz $^1$H NMR spectrum of coruscanone A (1) in $C_6D_6$ (1a/1b: ~1/1) after sitting in the NMR tube at r.t. for 24 hr

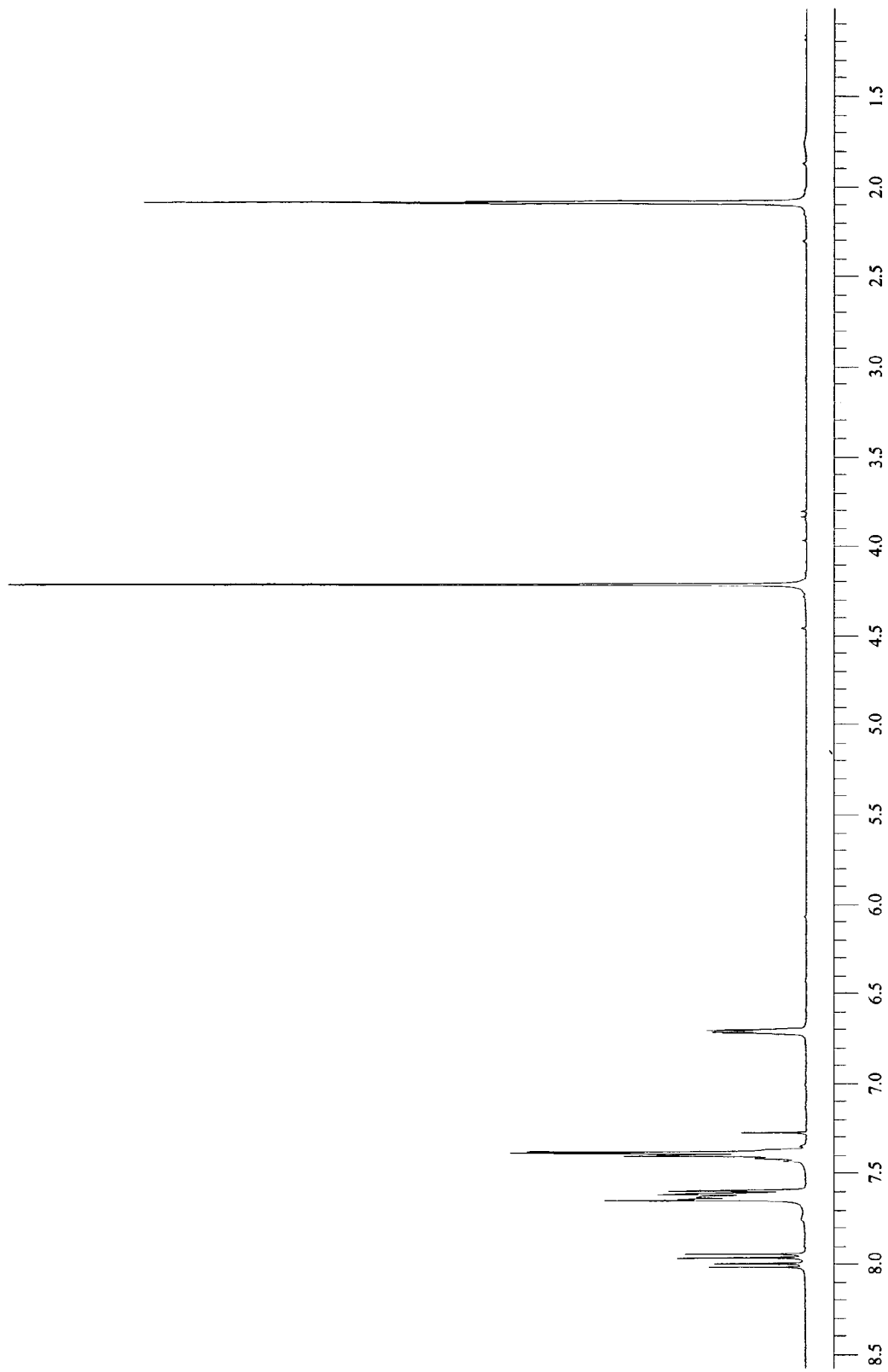
Figure 3. 300 MHz $^1$H NMR spectrum of coruscanone A (1) in CDCl$_3$ (*1a*/*1b*: ~1/1) after sitting in the NMR tube at r.t. for 12 hrs

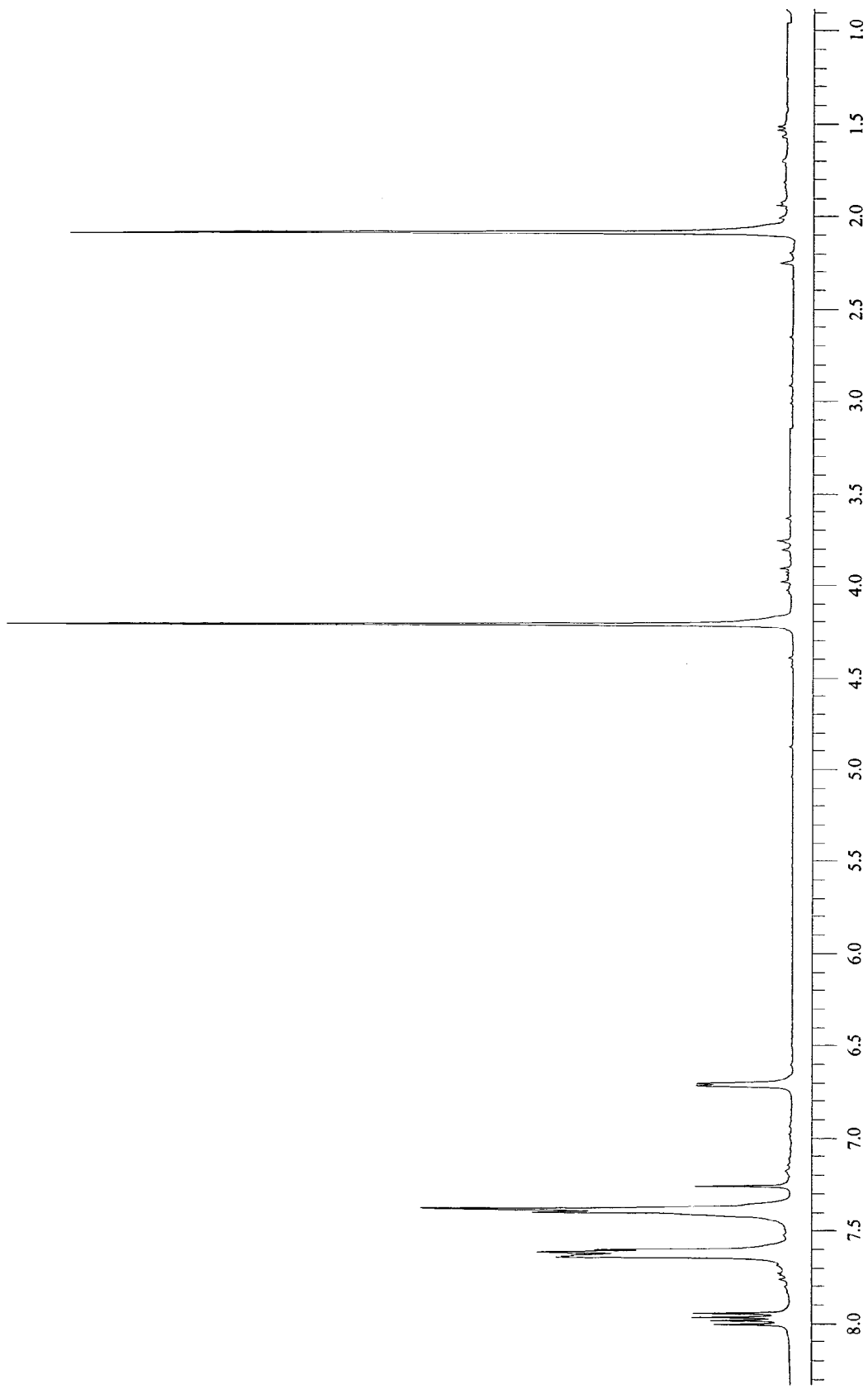
*Figure 4. 400 MHz $^1$H NMR spectrum of synthetic coruscanone A (1) in CDCl$_3$ (1a/1b: ~1/1) after sitting in the NMR tube at r.t. for 12 hrs*

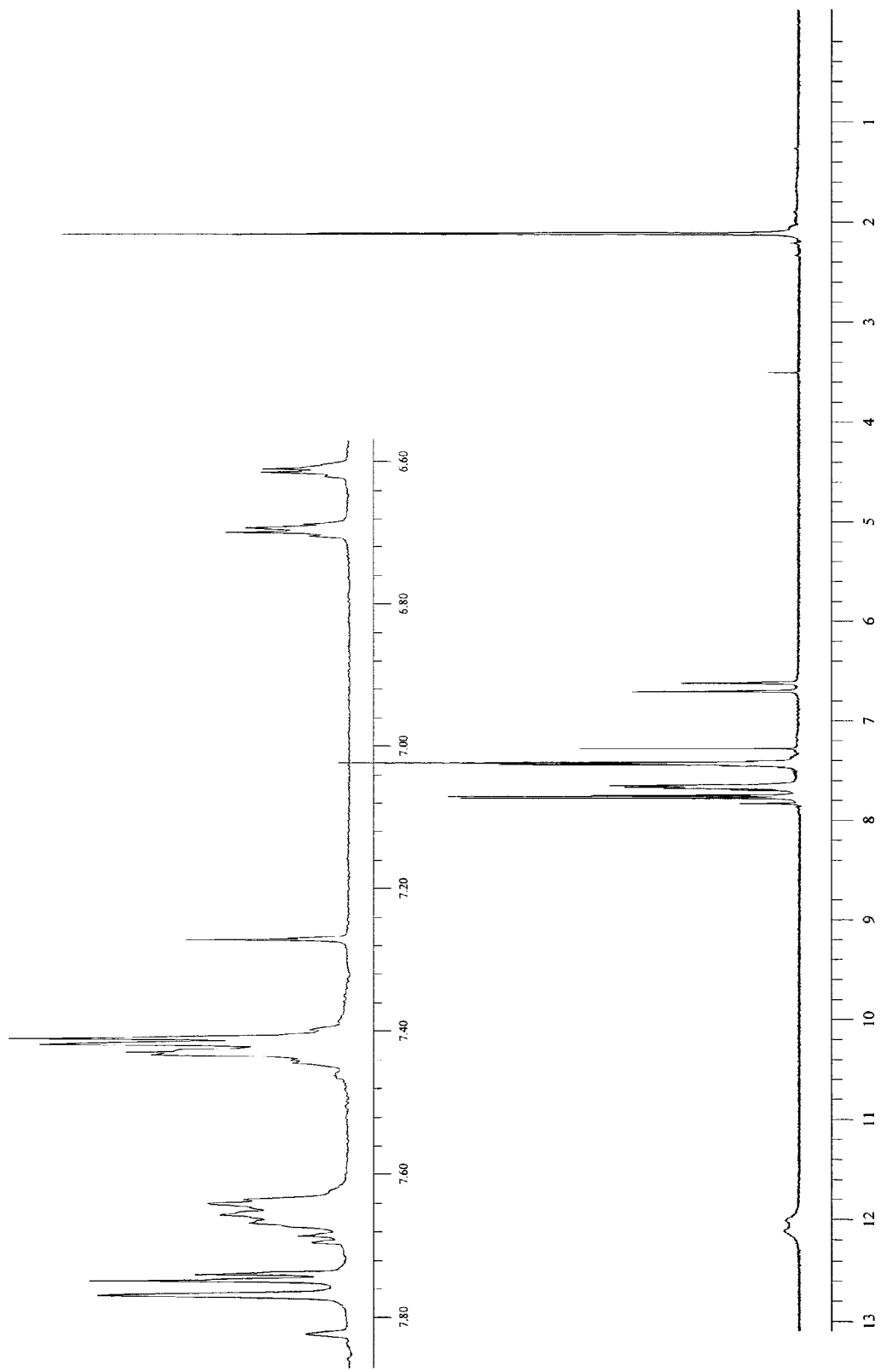
*Figure 5. 300 MHz $^1$H NMR spectrum of coruscanone B (2) in CDCl$_3$ (2a/2b: ~1/1.2) after sitting in the NMR tube for 24 hr at r.t.*

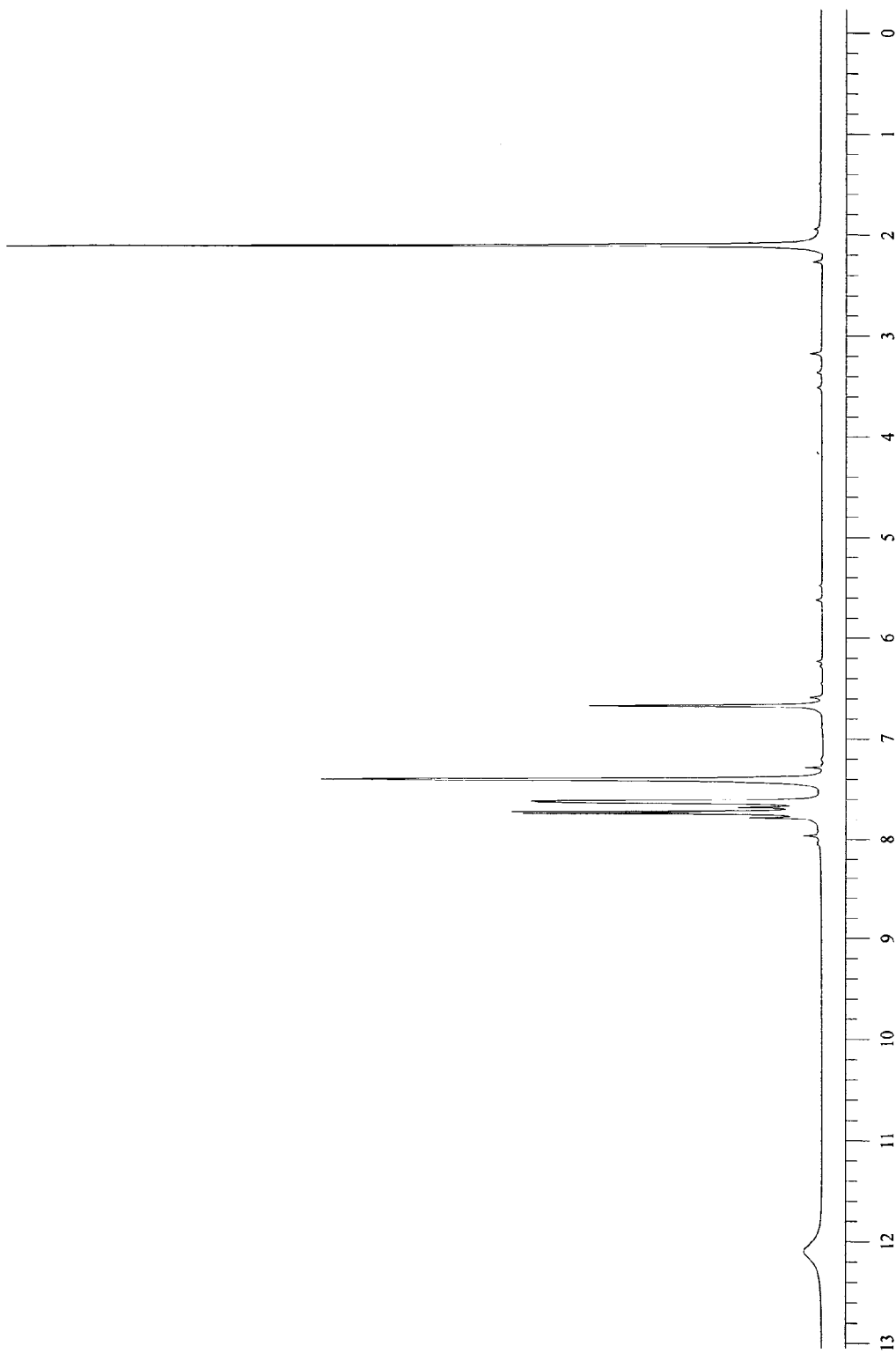
Figure 6. 400 MHz $^1$H NMR spectrum of synthetic coruscanone B (2) in CDCl$_3$ (predominant 2b) at r.t.

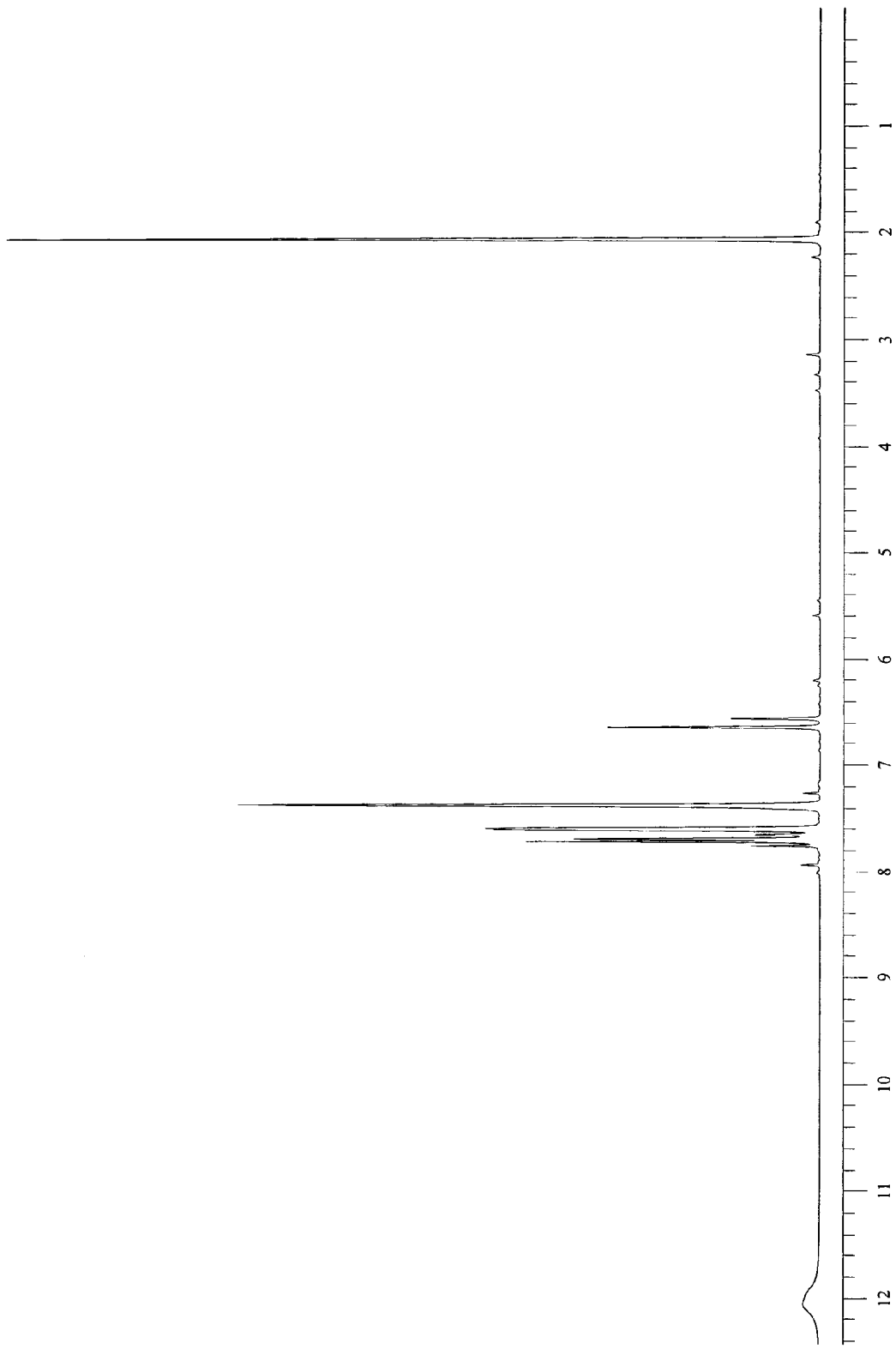
Figure 7. 400 MHz $^1$H NMR spectrum of synthetic coruscanone B (2) in CDCl$_3$ (2b/2a: ~2.4:1) after sitting in the NMR tube at r.t. for 5 hr

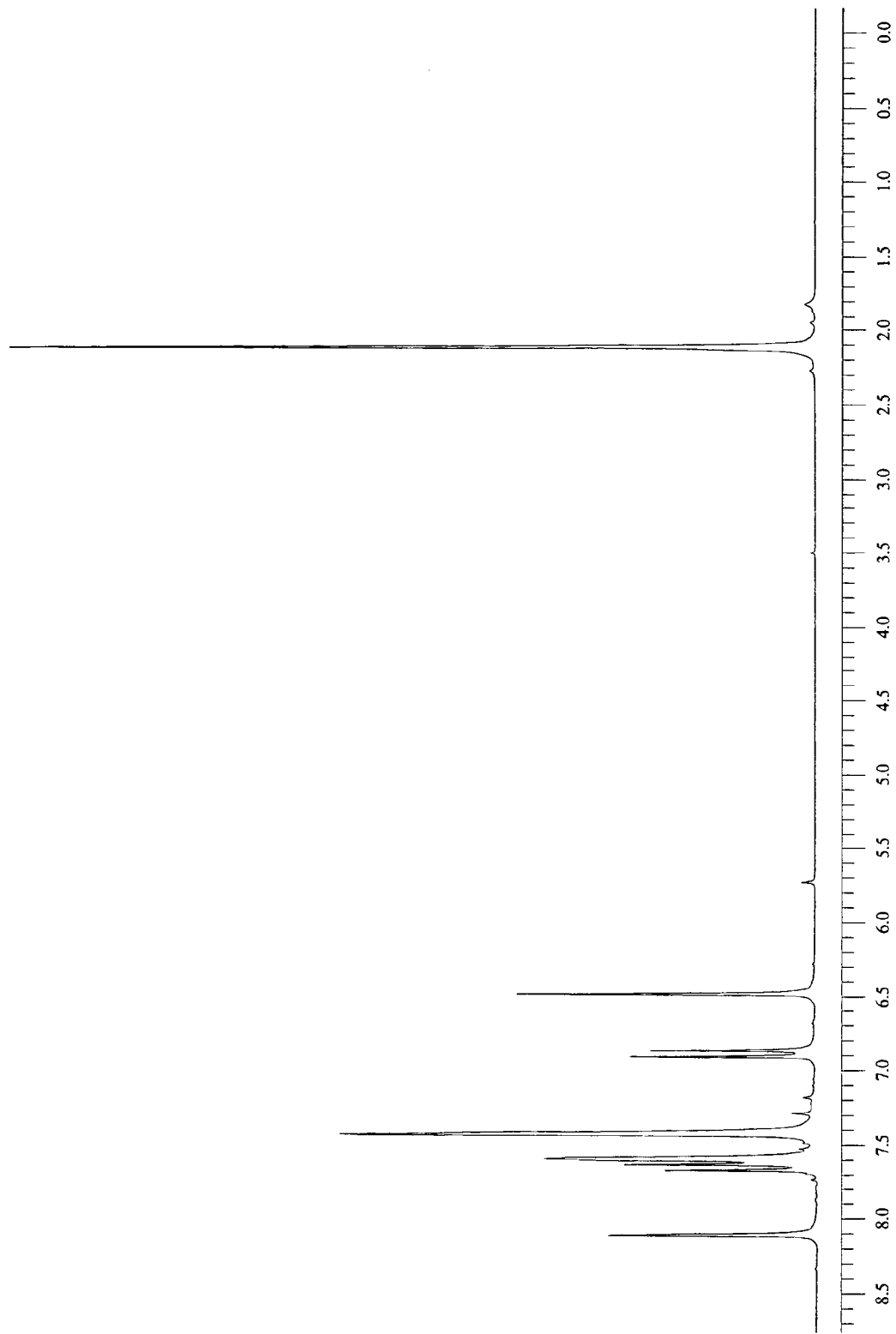
Figure 8. 400 MHz $^1$H NMR spectrum of ylidenebutenolide 5 in CDCl$_3$.

CYCLOPENTENEDIONE ANTIFUNGAL COMPOUNDS AND METHODS FOR THEIR USE

PRIORITY

This application claims benefit under 35 U.S.C. § 119(e) to U.S. Patent Application No. 60/557,323, filed Mar. 29, 2004, the contents of which are incorporated herein by reference in their entirety.

GOVERNMENT SUPPORT

This invention was made with support from Grant Number AI27094 from the National Institutes of Health National Institute of Allergy and Infectious Diseases, Division of AIDS, and USDA Agricultural Research Service Specific Cooperative Agreement No. 58-6408-2-0009. The Government has rights to this invention.

FIELD OF THE INVENTION

The present invention relates to the field of cyclopentenedione compounds and methods of use thereof. More specifically, the methods include their use as antifungal agents. The compounds of the present invention include coruscanone A and B, described herein. The antifungal potency of an embodiment of the present invention, coruscanone A, against *Candidau albicans* is comparable to or stronger than those of positive control drugs, amphotericin B and fluconazole. In addition, it inhibits fluconazole-resistant *C. albicans* strains.

Compounds of the present invention may be used as an antifungal agents or as a template for preparing a new class of antifungal agents, including those for use for the treatment of life-threatening candidiasis associated with immuno-compromised patients.

BACKGROUND OF THE INVENTION

Natural acylcyclopentenediones comprise only a few compounds with limited occurrence. Regarding the biological activity of this unique class of compounds, methyllinderone was cytotoxic against several cancer cell lines, while methyllucidone showed moderately antifungal activity against wheat leaf rust caused by *Puccinia recondite*. A significant work in this regard was the identification of the synthetic analog 2-(1-methoxy-3-phenyl-2-propenylidene)-cyclopent-4-ene-1,3-dione as a potent inhibitor of human chymase, a potential drug target associated with cardiovascular diseases and chronic inflammation following fibrosis. The synthesis of this compound was inspired by the natural product methyllinderone, a moderate inhibitor of the enzyme identified from the screening of a compound library. It is noted, however, that the cyclopent-4-ene- and cyclopentane-1,3-dione structural moieties are present in a number of synthetic compounds with therapeutic applications or potential.

The present inventors have discovered that the ethanol extract of the whole Peruvian plant, *Piper coruscans* H.B. & K. exhibits significant antifungal activity against *Candida albicans* ($IC_{50} < 2$ µg/mL). A subsequent antifungal bioassay-guided fractionation of this extract led to identification of novel antifungal cyclopentenedione derivatives of the present invention.

OBJECTS AND SUMMARY OF THE INVENTION

An aspect of the present invention is to provide novel compounds and compositions that can be used as safe, effective antifungal agents (for mammals, including humans).

Another aspect of the present invention is to provide compounds or compositions with antifungal potency against *Candida albicans*.

Another aspect of the present invention is to provide compounds or compositions that have an antifungal potency against fluconazole-resistant *Candida albicans* strains of fungi.

Another aspect of the present invention is to provide compounds and compositions that are useful agents in combating fungi.

Another aspect of the present invention is to provide substantially pure antifungal compounds from extracts from *Piper coruscans*. In this context, substantially pure is from about 90% to about 99%.

Another aspect of the present invention is to provide a method for treating a fungal condition in a patient in need thereof comprising administering a antifungal effective amount of a compound or composition of the present invention.

Another aspect of the present invention is to provide a template for preparing classes of antifungal agents for use in treating patients in need thereof.

Another aspect of the present invention is to provide an antifungal compound or composition that has action as a plant protection agent.

Another aspect of the present invention is to provide a method of treating or preventing fungal activity in plants.

Another aspect of the present invention is to provide an agrochemical composition, which comprises a compound of the present invention and an agriculturally acceptable carrier.

Another aspect of the present invention provides an agrochemical composition, which comprises a compound of the present invention and a second active ingredient such as a herbicide, insecticide, or fertilizer.

These and other objects will be apparent when reviewing this disclosure and claims.

One embodiment of the present invention is a compound of the following formula:

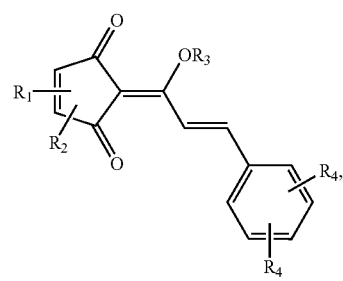

where $R_{1-4}$ are each independently H, alkyl, methyl, acyl, halogen, phenyl; provided that when $R_3$ is methyl and each $R_4$ is H, $R_1$ and $R_2$ are not both H; and provided that when $R_3$ and $R_4$ are both H, $R_1$ and $R_2$ are not both methyl; stereoisomers and pharmaceutically acceptable salts thereof.

A preferred embodiment of the present invention is a compound of the following formula:

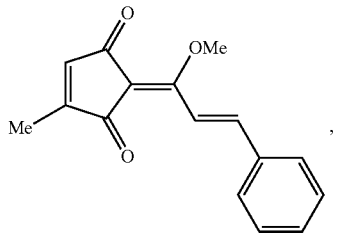

and stereoisomers and pharmaceutically acceptable salts thereof.

Another embodiment of the present invention is a compound of the following formula:

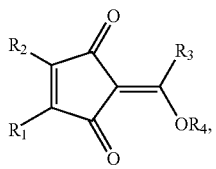

wherein $R_1$ and $R_2$ are independently H, $CH_3$, alkyl, halogen, phenyl;

$R_3$ is alkyl, alkenyl, alkynyl, styryl, heterocycle, cycloalkyl, aryl, alkylcycloalkyl, alkylheterocycle, alkylaryl;

$R_4$ is alkyl, alkenyl, acyl, glycosyl, phosphate, sulphate;

provided that when one of $R_1$ or $R_2$ is methyl and the other one of $R_1$ or $R_2$ is H, then $R_3$ and $R_4$ are not both methyl;

and stereoisomers and pharmaceutically acceptable salts thereof. In these and other embodiments disclosed herein, the variables may be the same or different.

The compounds of the present invention may, of course, be in composition form. Additionally, the compound of the present invention have broad utility as antifungal compounds.

BRIEF DESCRIPTION OF THE DRAWINGS

FIG. 1 shows a 300 MHz $^1$H NMR spectrum of coruscanone A (1) in $C_6D_6$ (1a/1b: ~5/1).

FIG. 2 shows a 300 MHz $^1$H NMR spectrum of coruscanone A (1) in $C_6D_6$ (1a/1b: ~1/1) after sitting in the NMR tube at r.t. for 24 hrs.

FIG. 3 shows a 300 MHz $^1$H NMR spectrum of coruscanone A (1) in $CDCl_3$ (1a/1b: ~1/1) after sitting in the NMR tube at r.t. for 12 hrs.

FIG. 4 shows a 400 MHz $^1$H NMR spectrum of synthetic coruscanone A (1) in $CDCl_3$ (1a/1b: ~1/1) after sitting in the NMR tube for at r.t. 12 hrs.

FIG. 5 shows a 300 MHz $^1$H NMR spectrum of coruscanone B (2) in $CDCl_3$ (2a/2b: ~1/1.2) after sitting in the NMR tube at r.t. for 24 hr.

FIG. 6 shows a 400 MHz $^1$H NMR spectrum of synthetic coruscanone B (2) in $CDCl_3$ (predominant 2b) at r.t.

FIG. 7 shows a 400 MHz $^1$H NMR spectrum of synthetic coruscanone B (2) in $CDCl_3$ (2b/2a: ~2.4:1) after sitting in the NMR tube at r.t for 5 hr.

FIG. 8 shows a 400 MHz $^1$H NMR spectrum of ylidenebutenolide 5 in $CDCl_3$.

DETAILED DESCRIPTION OF THE INVENTION

The present invention includes compounds and compositions of the following formula:

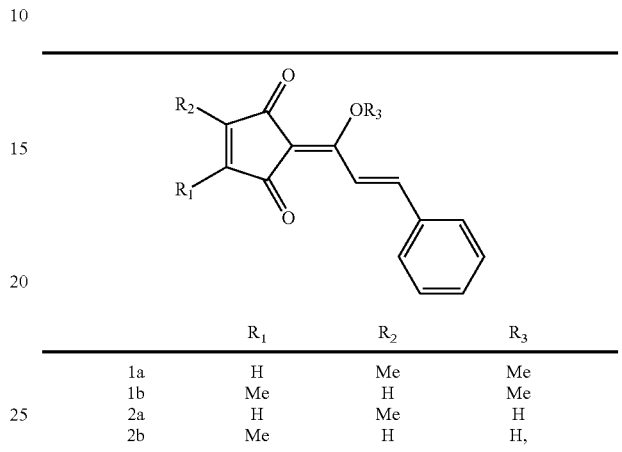

|    | $R_1$ | $R_2$ | $R_3$ |
|----|-------|-------|-------|
| 1a | H     | Me    | Me    |
| 1b | Me    | H     | Me    |
| 2a | H     | Me    | H     |
| 2b | Me    | H     | H,    | and stereoisomers, analogs, and pharmaceutically acceptable salts thereof.

The present invention further includes compositions that comprise the compounds of the present invention.

Also included are pharmaceutically acceptable derivatives of the foregoing compounds and compositions, where the phrase "pharmaceutically acceptable derivative" denotes any pharmaceutically acceptable salt, ester, or salt of such ester, of such compound, or any other adduct or derivative which, upon administration to a patient, is capable of providing (directly or indirectly) a compound as described herein, or a metabolite or residue thereof, with antifungal properties. Pharmaceutically acceptable derivatives thus include pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest.

The compounds of the present invention, and the pharmaceutically acceptable salts including acid addition salts thereof are useful agents in combating fungi. For example, compounds and compositions of the present invention are active against a wide variety of fungi such as, for example, *Microsporum canis*, *Ctenomyces mentagrophytes*, *Trichophyton rubrum*, *Phialophora verrucosa*, *Cryptococcus neoformans*, *Candida tropicalis*, *Candida albicans*, *Candida glabrata*, *Candida krusei*, *Candida pseudotropicalis*, *Candida parapsilosis*, *Aspergillus fumigatus*, *Aspergillus flavus*, *Mucor* species, *Sporotricum schenckii* and *Saprolegnia* species, etc.

In view of their potent (local as well as systemic) antimicrobial activity the compounds of this invention are useful in methods that cause or promote the destruction or prevention of the growth of fungi and more particularly they can effectively be used in the treatment of patients (human and animal) suffering from such microorganisms.

The compounds of the present invention also include the following:
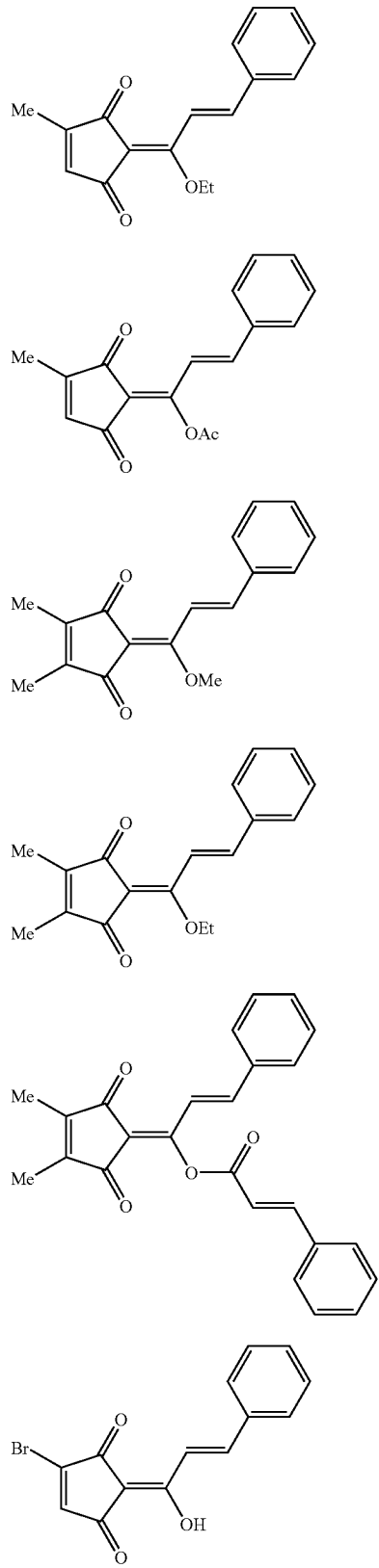
Additionally, compounds of the present invention include the following:
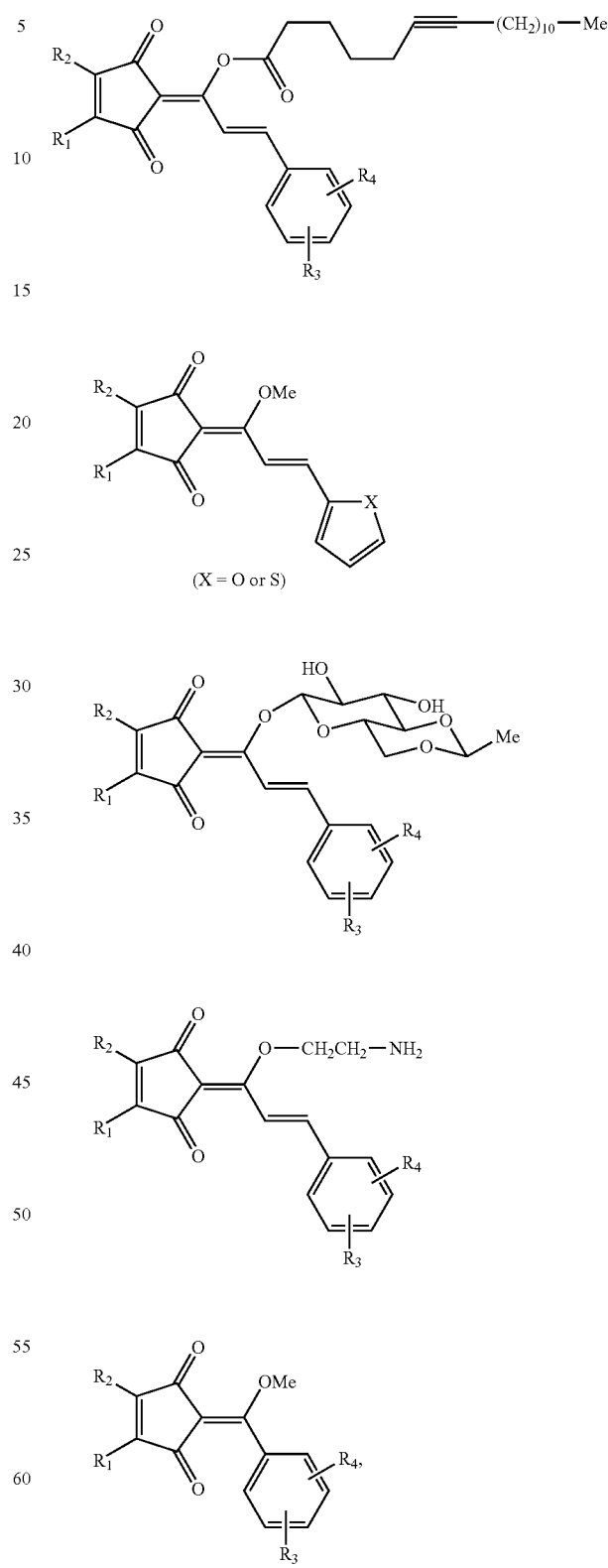
wherein $R_1$, $R_2$, $R_3$ and $R_4$ are as defined above and may be the same or different.

Additionally, compounds of the present invention include the following:

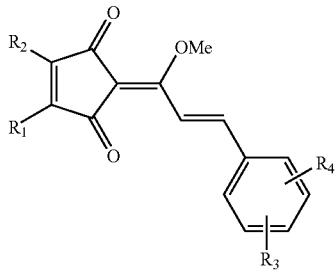

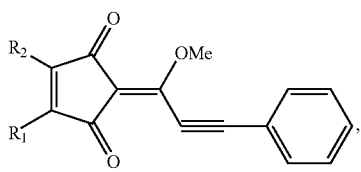

wherein $R_1$ and $R_2$ are defined above, but with the proviso that where $R_1$ and $R_2$ are not both H.

As discussed further below, the compounds of the present invention may be used in pharmaceutical compositions, comprising a compound of the present invention and a pharmaceutically acceptable carrier.

The term composition, when used herein, as in pharmaceutical or agricultural composition, is intended to encompass a product comprising the active ingredient(s), and the inert ingredient(s) that make up the carrier, as well as any product which results, directly or indirectly, from combination, complexation, aggregation or other interactions of any two or more of the active ingredient(s) and/or the inert ingredient(s) or from dissociation of one or more of the active ingredient(s) and/or the inert ingredient(s), or from other types of reactions of one or more of the active ingredient(s) and/or the inert ingredient(s).

One embodiment of the present invention is a method of treating, controlling, or preventing fungal activity in plants or mammals, comprising the administration of an effective amount of a compound of the following formula:

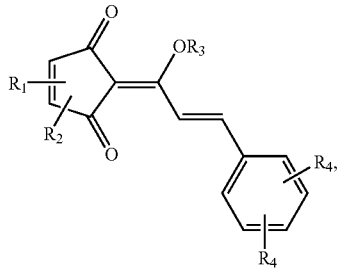

wherein $R_{1-4}$ are independently H, alkyl, methyl, halo, phenyl.

Another embodiment of the present invention is a method of treating, controlling, or preventing fungal activity in plants or mammals, comprising the administration of an effective amount a compound of the following formula:

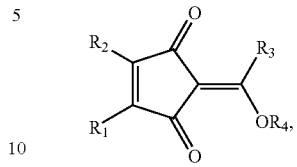

wherein $R_1$ and $R_2$ are independently H, $CH_3$, alkyl, halogen, phenyl;

$R_3$ is alkyl, alkenyl, alkynyl, styryl, heterocycle, cycloalkyl, aryl, alkylcycloalkyl, alkylheterocycle, alkylaryl;

$R_4$ is H, alkyl, alkenyl, acyl, glycosyl; and stereoisomers, and pharmaceutically acceptable salts thereof. Each variable may be the same or different.

In one embodiment, the compound is of the following formula:

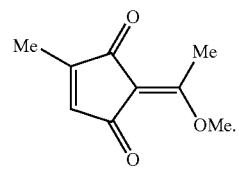

The phrase "effective amount" or similar phrases used herein mean the amount of a compound/composition of the present invention that inhibits, prevents, and/or controls the propagation and/or growth of a fungal species relative to an untreated control.

The term controlling includes prophylactic use (i.e. to protect against infection) and curative use (i.e. to eradicate infection).

As used herein, the term alkyl or alkyl group is to be understood in the broadest sense to mean hydrocarbon residues which can be linear, i.e., straight-chain, or branched, and can be acyclic or cyclic residues (i.e., cycloalkyl) or comprise any combination of acyclic and cyclic subunits. Further, the term alkyl as used herein expressly includes saturated groups as well as unsaturated groups which latter groups contain one or more, for example, one, two, or three, double bonds and/or triple bonds.

All these statements also apply if an alkyl group carries substituents or occurs as a substituent on another residue, for example, in an alkyloxy residue, or an arylalkylamino residue. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl, and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl, or tert-pentyl.

Unsaturated alkyl residues are, for example, alkenyl residues such as vinyl, 1-propenyl, 2-propenyl(=allyl), 2-butenyl, 3-butenyl, 2-methyl-2-butenyl, 3-methyl-2-butenyl, 5-hexenyl, or 1,3-pentadienyl, or alkynyl residues such as ethynyl, 1-propynyl, 2-propynyl(=propargyl), or 2-butynyl. Alkyl residues can also be unsaturated when they are substituted.

Examples of cyclic alkyl residues are cycloalkyl residues containing 3, 4, 5, 6, 7, or 8 ring carbon atoms like cyclopropyl, cyclobutyl, cyclopentyl, cyclohexyl, cycloheptyl, or cyclooctyl which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, cyclohexylmethyl-, cycloheptylmethyl-, cyclooctylmethyl-, 1-cyclopropylethyl-, 1-cyclobutylethyl-, 1-cyclopentylethyl-, 1-cyclohexylethyl-, 1-cycloheptylethyl-, 1-cyclooctylethyl-, 2-cyclopropylethyl-, 2-cyclobutylethyl-, 2-cyclopentylethyl-, 2-cyclohexylethyl-, 2-cycloheptylethyl-, 2-cyclooctylethyl-, 3-cyclopropylpropyl-, 3-cyclobutylpropyl-, 3-cyclopentylpropyl-, 3-cyclohexylpropyl-, 3-cycloheptylpropyl-, or 3-cyclooctylpropyl- in which groups the cycloalkyl subgroup as well as acyclic subgroup also can be unsaturated and/or substituted.

Of course, a group like $(C_1-C_8)$-alkyl is to be understood as comprising, among others, saturated acyclic $(C_1-C_8)$-alkyl, $(C_3-C_8)$-cycloalkyl, cycloalkyl-alkyl groups like $(C_3-C_7)$— cycloalkyl-$(C_1-C_5)$-alkyl- wherein the total number of carbon atoms can range from 4 to 8, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, $(C_3-C_4)$-cycloalkyl, cyclopropyl-methyl-, and unsaturated $(C_2-C_4)$-alkyl like $(C_2-C_4)$-alkenyl or $(C_2-C_4)$-alkynyl. Thus, cycloalkyl is understood to include alkylcycloalkyl groups.

Unless stated otherwise, the term alkyl preferably comprises acyclic saturated hydrocarbon residues containing from 1 to 6 carbon atoms which can be linear or branched, acyclic unsaturated hydrocarbon residues containing from 2 to 6 carbon atoms which can be linear or branched like $(C_2-C_6)$-alkenyl and $(C_2-C_6)$-alkynyl, and cyclic alkyl groups containing from 3 to 8 ring carbon atoms, in particular from 3 to 6 ring carbon atoms. A particular group of saturated acyclic alkyl residues is formed by $(C_1-C_4)$-alkyl residues like methyl, ethyl, n-propyl, isopropyl, n-butyl, isobutyl, sec-butyl, and tert-butyl.

The alkyl groups of the present invention can in general be unsubstituted or substituted by one or more, for example, one, two, three, or four, identical or different substituents. Any kind of substituents present in substituted alkyl residues can be present in any desired position provided that the substitution does not lead to an unstable molecule. Examples of substituted alkyl residues are alkyl residues in which one or more, for example, 1, 2, 3, 4, or 5, hydrogen atoms are replaced with halogen, nitrogen, sulfur or oxygen atoms.

Examples of substituted cycloalkyl groups are cycloalkyl groups which carry as substituent one or more, for example, one, two, three, or four, identical or different acyclic alkyl groups, for example, acyclic $(C_1-C_4)$-alkyl groups like methyl groups. Examples of substituted cycloalkyl groups are 4-methylcyclohexyl, 4-tert-butylcyclohexyl, or 2,3-dimethylcyclopentyl.

Examples of substituted cycloalkyl groups are cycloalkyl groups which carry as substituent one or more, for example, one, two, three, or four, identical or different acyclic alkyl groups, for example, acyclic $(C_1-C_4)$-alkyl groups like methyl groups. Examples of substituted cycloalkyl groups are 4-methylcyclohexyl, 4-tert-butylcyclohexyl, or 2,3-dimethylcyclopentyl.

The term aryl refers to a monocyclic or polycyclic hydrocarbon residue in which at least one carbocyclic ring is present. In a $(C_6-C_{14})$-aryl residue from 6 to 14 ring carbon atoms are present. Examples of $(C_6-C_{14})$-aryl residues are phenyl, naphthyl, biphenylyl, fluorenyl, or anthracenyl. Examples of $(C_6-C_{10})$-aryl residues are phenyl or naphthyl. Unless stated otherwise, and irrespective of any specific substituents bonded to aryl groups, aryl residues including, for example, phenyl, naphthyl, and fluorenyl, can in general be unsubstituted or substituted by one or more, for example, one, two, three, or four, identical or different substituents. Aryl residues can be bonded via any desired position, and in substituted aryl residues the substituents can be located in any desired position.

In monosubstituted phenyl residues, the substituent can be located in the 2-position, the 3-position, or the 4-position, the 3-position and the 4-position being preferred. If a phenyl group carries two substituents, they can be located in 2,3-position, 2,4-position, 2,5-position, 2,6-position, 3,4-position, or 3,5-position. In phenyl residues carrying three substituents, the substituents can be located in 2,3,4-position, 2,3,5-position, 2,3,6-position, 2,4,5-position, 2,4,6-position, or 3,4,5-position. Naphthyl residues can be 1-naphthyl and 2-naphthyl. In substituted naphthyl residues, the substituents can be located in any positions, for example, in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position. Biphenylyl residues can be 2-biphenylyl, 3-biphenylyl, or 4-biphenylyl. Fluorenyl residues can be 1-, 2-, 3-, 4-, or 9-fluorenyl. In monosubstituted fluorenyl residues, bonded via the 9-position the substituent is preferably present in the 1-, 2-, 3-, or 4-position.

Unless stated otherwise, substituents that can be present in substituted aryl groups are, for example, $(C_1-C_8)$-alkyl, in particular $(C_1-C_4)$-alkyl, such as methyl, ethyl, or tert-butyl, hydroxy, $(C_1-C_8)$-alkyloxy, in particular $(C_1-C_4)$-alkyloxy, such as methoxy, ethoxy, or tert-butoxy, methylenedioxy, ethylenedioxy, F, Cl, Br, I, cyano, nitro, trifluoromethyl, trifluoromethoxy, hydroxymethyl, formyl, acetyl, amino, mono- or di-$(C_1-C_4)$-alkylamino, $((C_1-C_4)$-alkyl)carbonylamino like acetylamino, hydroxycarbonyl, $((C_1-C_4)$-alkyloxy)carbonyl, carbamoyl, optionally substituted phenyl, benzyl optionally substituted in the phenyl group, optionally substituted phenoxy, or benzyloxy optionally substituted in the phenyl group.

The above statements relating to aryl groups correspondingly apply to divalent residues derived from aryl groups, i.e., to arylene groups like phenylene which can be unsubstituted or substituted 1,2-phenylene, 1,3-phenylene, or 1,4-phenylene, or naphthalene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl, or 2,7-naphthalenediyl.

The above statements also correspondingly apply to the aryl subgroup in arylalkyl-groups. Examples of arylalkyl-groups which can also be unsubstituted or substituted in the aryl subgroup as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, or 9-fluorenylmethyl.

Of course, where terms are used in combination, the definition for each individual part of the combination applies unless defined otherwise.

Acetyl is defined as any group comprising an acetyl radical (CH$_3$CO—). Styryl is defined as 2-phenyl-vinyl (PhCH=CH—).

The "heterocycle" group comprises groups containing 3, 4, 5, 6, 7, 8, 9, or 10 ring atoms in the parent monocyclic or bicyclic heterocyclic ring system. In monocyclic heterocycle groups, the heterocyclic ring preferably is a 3-membered, 4-membered, 5-membered, 6-membered, or 7-membered ring, particularly preferably, a 5-membered or 6-membered ring. In bicyclic heterocycle groups, preferably two fused rings are present, one of which is a 5-membered ring or 6-membered heterocyclic ring and the other of which is a 5-membered or 6-membered heterocyclic or carbocyclic ring, i.e., a bicyclic heterocycle ring preferably contains 8, 9, or 10 ring atoms, more preferably 9 or 10 ring atoms.

The heterocycle groups of the present invention comprise saturated heterocyclic ring systems which do not contain any double bonds within the rings, as well as mono-unsaturated and poly-unsaturated heterocyclic ring systems which contain one or more, for example, one, two, three, four, or five, double bonds within the rings provided that the resulting system is stable. Unsaturated rings may be non-aromatic or aromatic, i.e., double bonds within the rings in the heterocycle group may be arranged in such a manner that a conjugated pi electron system results. Aromatic rings in a heterocycle group may be 5-membered or 6-membered rings, i.e., aromatic groups in a heterocycle group contain 5 to 10 ring atoms. Aromatic rings in a heterocycle group thus comprise 5-membered and 6-membered monocyclic heterocycles and bicyclic heterocycles composed of two 5-membered rings, one 5-membered ring, and one 6-membered ring, or two 6-membered rings. In bicyclic aromatic groups in a heterocycle group, one or both rings may contain heteroatoms. Aromatic heterocycle groups may also be referred to by the customary term heteroaryl for which all the definitions and explanations above and below relating to heterocycle correspondingly apply.

Unless stated otherwise, in the heterocycle groups and any other heterocyclic groups, preferably 1, 2, 3, or 4 identical or different ring heteroatoms selected from nitrogen, oxygen, and sulfur are present. Particularly preferably, in these groups 1 or 2 identical or different ring heteroatoms selected from nitrogen, oxygen, and sulfur are present. The ring heteroatoms can be present in any desired number and in any position with respect to each other provided that the resulting heterocyclic system is known in the art and is stable and suitable as a subgroup in a drug substance. Examples of parent structures of heterocycles from which the heterocycle group can be derived are aziridine, oxirane, thiirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, or pteridine, as well as ring systems which result from the listed heterocycles by fusion (or condensation) of a carbocyclic ring, for example, benzo-fused, cyclopenta-fused, cyclohexa-fused, or cyclohepta-fused derivatives of these heterocycles.

The heterocycle residue may be bonded via any ring carbon atom, and in the case of nitrogen heterocycles, via any suitable ring nitrogen atom. Thus, for example, a pyrrolyl residue can be 1-pyrrolyl, 2-pyrrolyl, or 3-pyrrolyl, a pyrrolidinyl residue can be 1-pyrrolidinyl (=pyrrolidino), 2-pyrrolidinyl, or 3-pyrrolidinyl, a pyridyl residue can be 2-pyridyl, 3-pyridyl, or 4-pyridyl, and a piperidinyl residue can be 1-piperidinyl(=piperidino), 2-piperidinyl, 3-piperidinyl, or 4-piperidinyl. Furyl can be 2-furyl or 3-furyl, thienyl can be 2-thienyl or 3-thienyl, imidazolyl can be 1-imidazolyl, 2-imidazolyl, 4-imidazolyl, or 5-imidazolyl, 1,3-oxazolyl can be 1,3-oxazol-2-yl, 1,3-oxazol-4-yl, or 1,3-oxazol-5-yl, 1,3-thiazolyl can be 1,3-thiazol-2-yl, 1,3-thiazol-4-yl, or 1,3-thiazol-5-yl, pyrimidinyl can be 2-pyrimidinyl, 4-pyrimidinyl(=6-pyrimidinyl), or 5-pyrimidinyl, and piperazinyl can be 1-piperazinyl(=4-piperazinyl=piperazino) or 2-piperazinyl. Indolyl can be 1-indolyl, 2-indolyl, 3-indolyl, 4-indolyl, 5-indolyl, 6-indolyl, or 7-indolyl. Similarly, benzimidazolyl, benzoxazolyl, and benzothiazolyl residues can be bonded via the 2-position and via any of the positions 4, 5, 6, and 7, benzimidazolyl also via the 1-position.

Unless stated otherwise, and irrespective of any specific substituents bonded to heterocycle groups or any other heterocyclic groups which are indicated in the definition of compounds of the present invention, the heterocycle group can be unsubstituted or substituted on ring carbon atoms with one or more, for example, one, two, three, four, or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl, 1-hydroxyethyl, or 2-hydroxyethyl, methylenedioxy, ethylenedioxy, formyl, acetyl, cyano, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, or benzyloxy optionally substituted in the phenyl group. The substituents can be present in any desired position provided that a stable molecule results.

Preferred alkylheterocycle substituents include the following:

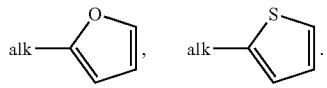

All compounds disclosed herein are assumed to include pharmaceutically acceptable salt forms. The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The present invention also comprises all pharmaceutically acceptable compositions that comprise a compound of the present invention. The definition of "pharmaceutically acceptable" is meant to encompass any carrier, which does not substantially interfere with effectiveness of the active ingredient and that is not toxic to the host to which it is administered. For example, for parenteral administration, the compounds of the present invention may be formulated in a unit dosage form for injection in vehicles such as saline, dextrose solution, etc. that may contain additives such as those that maintain stability.

In view of their antifungal activity, compounds of the present invention are useful for the treatment, control, and/or prevention of a variety of fungal infections in mammals, including human beings. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal diaper rash, candida vulvitis, candida balanitis and otitis oxterna. They may also be used as prophylactic agents to prevent systemic and topical fungal infections. Use as prophylactic agents may, for example, be appropriate as part of a selective gut decontamination regimen in the prevention of infection in immuno-compromised patients (e.g. AIDS patients, patients receiving cancer therapy or transplant patients). Prevention of fungal overgrowth during antibiotic treatment may also be desirable in some disease syndromes or iatrogenic states.

Coruscanone A (compound 1 of the present invention) has a molecular formula of $C_{16}H_{14}O_3$ by high resolution ESIMS. The $^1H$ NMR spectrum of 1 in benzene-$d_6$ at room temperature, which has a better resolution than in $CDCl_3$, displays a set of major peaks accompanied by corresponding less intense peaks with close chemical shifts in a ratio of approximately 5:1. When the NMR sample in benzene-$d_6$ was allowed to sit at room temperature for 24 hrs, two geometric isomers (1a, 1b) reached a ratio of almost 1:1, indicating similar energies of the two isomers in solution.

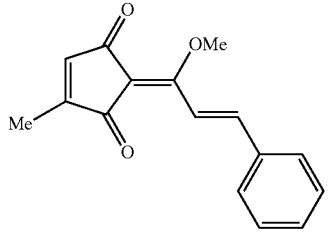

Compound 1

Coruscanone B (compound 2 of the present invention) displays $^1H$ and $^{13}C$ NMR spectra similar to those of 1. The spectra of 2 differs from those of 1 in that 2 possesses a hydroxyl group on the side chain instead of a methoxy group. This is supported by its high resolution ESIMS which gave a molecular formula of $C_{15}H_{12}O_3$. In $CDCl_3$, two geometric isomers appear in a ratio of approximately 1:1.2 after equilibrating in the NMR tube at room temperature for 24 hrs. The slight difference of the ratio of the two isomers results in a slight difference of the intensity of the $^1H$ and $^{13}C$ NMR signals. This facilitates identification of one set of stronger signals corresponding to the major isomer 2b from another set of weaker signals corresponding to the minor isomer 2a. Since within each isomer the carbonyl carbon that forms hydrogen bonding with the allylic hydroxy group should be deshielded, the key HMBC correlations of the methyl protons and H-4 with carbonyl carbons enable correlation of the NMR data with respective isomers. This information also facilitates the assignments of the NMR data for two isomers of compound 1.

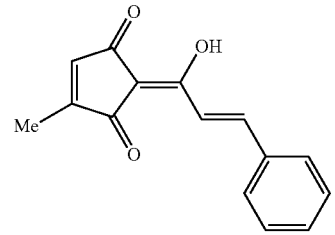

Compound 2

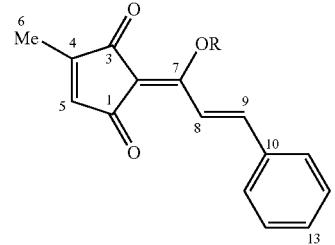

1a  R = Me
2a  R = H

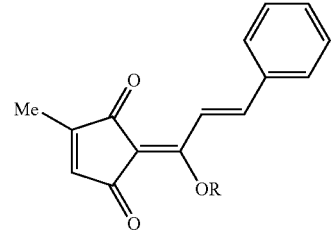

1b  R = Me
2b  R = H

Synthesis of Compounds of the Present Invention

An example of how compounds of the present invention can be made includes the following:

Scheme 1

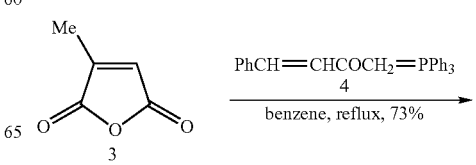

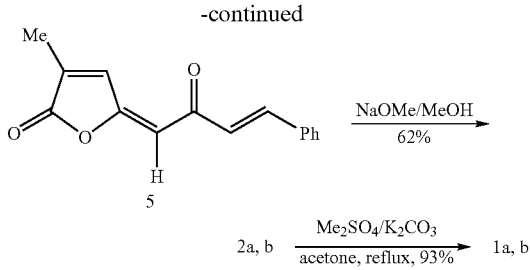

Synthesis of coruscanones A and B (compounds 1, 2) may be achieved by using a method for preparation of similar compounds (Scheme 1, for example). Thus, Wittig condensation of 2-methylmaleic anhydride (3) and cinnamoylmethylenetriphenylphosphorane (4) in hot benzene affords in a regio- and stereoselective manner 4-ylidenebutenolide 5. Treatment of 5 with MeONa in MeOH results in rearrangement to cylopentendione 2, which is further methylated with $Me_2SO_4$ in $K_2CO_3$/acetone to furnish 1.

TABLE 1

Antifungal Activity of Compounds 1 and 2 (MIC[a]/MFC[b], µg/mL)

| | Candida albicans ATCC 90028 | Cryptococcus neoformans ATCC 90113 |
|---|---|---|
| 1 | 0.78/1.56 | 6.25/6.25 |
| 2 | 50/NA[c] | NA[c]/NA[c] |
| Amphotericin B | 2.50/5.00 | 2.50/2.50 |

[a]Minimum Inhibitory Concentration.
[b]Minimum Fungicidal Concentration.
[c]Not active.

Coruscanones A and B are evaluated using bioassay protocols for in vitro antifungal activity against two major opportunistic pathogens associated with AIDS (Table 1). Compound 1 of the present invention especially show potent activity against C. albicans. Of particular significance is its strong activity against fluconazole-resistant C. albicans strains isolated from patients during fluconazole therapy. In the isolates showing up to 400-fold decreases in susceptibility to fluconazole, compound 1 of the present invention retains equivalent activity relative to the susceptible strains (Table 2).

TABLE 2

Antifungal Activity of Compound 1 against Azole-susceptible and Azole-resistant Candida albicans Strains [$IC_{50}$/$IC_{80}$/$IC_{95}$ (µg/mL)][a]

| C. albicans | 1 | Fluconazole |
|---|---|---|
| Isolate 1 | 0.60/1.00/1.50 | 1.00/1.50/2.00 |
| Isolate 2 | 0.90/1.00/1.50 | 1.00/5.00/10.00 |
| Isolate 5 | 0.40/0.60/0.70 | 7.50/10.00/10.00 |
| Isolate 8 | 0.90/1.00/1.50 | 15.00/20.00/25.00 |
| Isolate 1 | 0.45/0.60/0.75 | 0.10/0.20/100.00 |
| Isolate 17 | 0.30/0.90/1.50 | 40.00/95.00/NA[b] |

[a]Patient isolates: Isolate 1, azole-susceptible strain; Isolates 2, 5, 8, and 17, azole-resistant strains with increasing azole resistance. Growth inhibition concentrations represented by $IC_{50}$, $IC_{80}$, and $IC_{95}$ reflect a dose-effect curve.
[b]Not active at highest test concentration of 100 µg/mL.

Taking into account its antifungal potency and certain selectivity as well as its easy access by synthesis, compounds and compositions of the present invention may further serve as a template for a new class of antifungal agents, including ones used for the treatment of life-threatening disseminated candidiasis.

Mammalian Administration

While it is possible that, for use in therapy, compounds of the present invention may be administered as the raw chemical, it is preferable to present the active ingredient as a pharmaceutical composition. The pharmaceutical compositions of the present invention can be administered by one of ordinary skill in the art. In this regard, the pharmaceutical preparations can be delivered in several manners, specifically including topical applications and systemic applications.

The pharmaceutical compositions of the present invention may be administered by any known route, including parenterally and otherwise. This includes oral, nasal (via nasal spray or nasal inhaler), buccal, rectal, vaginal or topical administration. Administration may also be by orthotopic, intradermal subcutaneous, intramuscular, intraperitoneal or intravenous injection and/or infusion. Such compositions may be administered as pharmaceutically acceptable compositions that include pharmacologically acceptable carriers, buffers or other excipients. The phrase "pharmacologically acceptable" refers to molecular entities and compositions that do not produce an adverse, allergic or other untoward reaction when administered to a human. For treatment of conditions of the lungs, the preferred route is aerosol delivery to the lung via bronchoalveolar lavage or the like.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; or wetting agents such as sodium lauryl sulphate. The tablets which include chewable, dispersible or effervescent tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid.

For buccal administration the composition may take the form of tablets or lozenges formulated in conventional manner.

Intravenous injection and/or infusion may be used as a delivery route. In such embodiments, the compositions of the present invention may be administered gradually over a period of time ranging from 0.001 h to 100 h. In other embodiments, when administration of the pharmaceutical compositions of the present invention via intravenous injection and/or infusion is the preferred route, the pharmaceutical compositions of the present invention should be administered gradually over a period of time ranging from 0.1 h to 50 h. In other embodiments, when administration of the pharmaceutical compositions of the present invention via intravenous injection and/or infusion is the preferred route, the pharmaceutical compositions of the present invention should be administered gradually over a period of time ranging from 1 h to 10 h.

The mode of administration of a preparation of the present invention may determine the sites and cells in the organism to which a compound of the present invention will be delivered. Generally speaking, the compositions of the present invention will be administered in admixture with a pharmaceutical carrier selected with regard to the intended route of administration and standard pharmaceutical practice. For instance, delivery to a specific site may be most easily accomplished by topical application (if the infection is external, e.g., on areas such as eyes, skin, in ears, or on afflictions such as wounds or burns). Such topical applications may be in the form of creams, ointments, gels, emulsions, or pastes, for direct application to the afflicted area. Alternatively, the preparations may be injected parenterally, for example, intravenously, intramuscularly, or subcutaneously. For parenteral administration, they can be used, for example, in the form of a sterile aqueous solution which may contain other solutes, for example, enough salts or glucose to make the solution isotonic. Other uses, depending on the particular properties of the preparation, may be envisioned by those skilled in the art.

For therapeutic administration to humans, the prescribing physician will ultimately determine the appropriate dosage for a given human subject, and this can be expected to vary according to the age, weight, and response of the individual as well as the nature and severity of the patient's symptoms.

When the compounds of the present invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations. Examples of compounds for use with the compounds of the present invention include intraconazole, flucytosine, fluconazole, caspofungin or amphotericin B.

Agricultural Administration

With respect to the agricultural uses associated with the present invention, the compounds may be used as described in U.S. Pat. No. 3,852,470, incorporated herein by reference.

Furthermore, the compounds of the present invention may be used in accordance with U.S. Pat. No. 6,844,353, incorporated herein by reference. Thus, in general, it is desirable to apply the compounds of the present invention at concentrations in the range of 0.1 mM to 100 mM. However, exact dosages can be determined by one of ordinary skill in the art. With respect to the present invention, preferred dosages are amounts that will inhibit fungal growth under normal conditions of growth or storage, without causing necrotic damage to the plant, flowers or fruit.

The fungicide compositions according to the invention typically contain 0.5% to 95% by weight of active material. As described herein, unless otherwise specified, percentages are by weight.

The term "carrier" in the present text, designates an organic or inorganic material, natural or synthetic, with which the active material is combined in order to facilitate its application to the plant, fruit, seeds or soil. This carrier is therefore generally inert and must be agriculturally acceptable, particularly on the treated plant. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

The surface-active agent may be an emulsifying, dispersing or wetting agent of the ionic or nonionic type. The following may be mentioned by way of example: polyacrylic acid salts, lignosulphonic acid salts, phenolsulphonic or naphthalenesulphonic acid salts, polycondensates of ethylene oxide and fatty alcohols or fatty acids or fatty amines, substituted phenols (alkylphenols or arylphenols in particular), ester salts of sulphosuccinic acids, taurine derivatives (alkyltaurates in particular), phosphoric esters of alcohols or of polyoxyethylated phenols. The presence of at least one surface-active agent is essential given that the active material and/or the inert carrier are insoluble in water and that the vector agent of the application is water.

These compositions may also contain other ingredients such as, for example, protective colloids, adhesives, thickeners, thixotropic agents, penetrating agents, stabilizers, sequestrants, pigments, colorants and polymers, as determined by one of ordinary skill in the art.

More generally, the compositions according to the invention may be combined with all those solid or liquid additives found in the usual formulation procedures.

By way of solid composition forms, the following are included: powders for dusting or dispersing (with a content of active material (i.e. fungicide) which may be as high as 95%) and granules, particularly those obtained by extrusion, by compaction, by impregnation of a granulated carrier and by granulation from a powder (the content of active material in these granules being between 1% and 80% in the latter cases).

By way of liquid composition forms or forms intended to constitute liquid compositions on application, the following are included: solutions, in particular water-soluble concentrates, emulsifiable concentrates, emulsions, concentrated suspensions, aerosols, wettable powders (or spray powder) and pastes.

The emulsifiable or soluble concentrates generally comprise 10% to 80% of active material; the emulsions or solutions ready for application contain, 0.01% to 20% of active material.

For example, in addition to the solvent, the emulsifiable concentrates may contain when necessary, 2% to 20% of appropriate additives such as the stabilizers, surface-active agents, penetrating agents, corrosion inhibitors, colorants or adhesives previously mentioned.

From these concentrates, emulsions of any desired concentration, which are particularly suitable for application to leaves, seeds, flowers or fruit may be obtained by dilution with water.

The concentrated suspensions, which can also be applied by spraying, are prepared so as to obtain a stable fluid product which does not form deposits, and they normally contain from 10% to 75% of active material, 0.5% to 15% of surface-active agents, 0.1% to 10% of thixotropic agents, 0% to 10% of appropriate additives, such as pigments, colorants, antifoams, corrosion inhibitors, stabilizers, penetrating agents and adhesives and, by way of carrier, water or an organic liquid in which the active material is barely soluble or insoluble: some organic solid materials or inorganic salts may be dissolved in the carrier to help prevent sedimentation or as anti-freeze for water.

The wettable powders (or spray powders) are normally prepared so that they contain 20% to 95% of active material, and they normally contain, in addition to the solid carrier, from 0% to 5% of a wetting agent, 3% to 10% of a dispersing agent and, when necessary, from 0% to 10% of one or more stabilizers and/or other additives, such as pigments, colorants, penetrating agents, adhesives, or anti-coagulating agents, and the like. However, the exact composition can change as determined by one of ordinary skill in the art.

To obtain these spray powders or wettable powders, the active materials are thoroughly mixed in appropriate mixers with the additional substances and they are ground using mills or other appropriate grinders. Spray powders are thereby obtained having wettability and ability to form suspensions which are advantageous; they can be suspended in water at any desired concentration and these suspensions may be used very advantageously, in particular for application to plant leaves.

In place of the wettable powders, pastes may be prepared. The conditions and methods for the preparation and the use of these pastes are similar to those for wettable powders or spray powders.

The dispersable granules are normally prepared by agglomeration, in appropriate granulation systems, of the composition of the wettable powder type.

As already indicated, the dispersions and aqueous emulsions (e.g. the compositions obtained by diluting a wettable powder or an emulsifiable concentrate according to the invention with water), are included within the general scope of the present invention. The emulsions may be of the water-in-oil or oil-in-water types and they may have a thick pourable or spreadable consistency like that of a "mayonnaise".

The compositions according to the invention may be used in a preventive or curative capacity for combating fungi, particularly of the basidiomycete, ascomycete, adelomycete or imperfect fungi types, in particular rusts, oidium, eyespot, fusarioses, *Fusarium roseum, Fusarium nivale*, net blotch, leaf blotch, septoria spot, bunt, rhizoctonioses of vegetables and plants in general and, in particular, of cereals such as wheat, barley, rye, oats and their hybrids and also rice and maize.

The compositions according to the invention are active in particular against fungi particularly of the following types: *basidiomycetes, ascomycetes, adelomycetes* or *imperfect fungi* such as *Botrytis cinerea, Colletotrichum fragariae, Colletotrichum acutatum, Colletotrichum gloesporiodes, Erysiphe graminis, Puccinia recondita, Piricularia oryzae, Cercospora beticola, Puccinia striiformis, Erysiphe cichoracearum, Fusarium oxysporum* (melonis, for example), *Pyrenophora avenae, Septoria tritici, Venturia inaequalis, Whetzelinia sclerotiorum, Monilia laxa, Mycosphaerella fijiensis, Marssonina panettoniana, Alternaria solani, Aspergillus niger, Cercospora arachidicola, Cladosporium herbarum, Helminthosporium oryzae, Penicillium expansum, Pestalozzia* sp., *Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale, Rhizoctonia solani, phompsis obscurans.*

They are also active against the following fungi: *Acrostalagmus koningi, Alternaria, Colletotrichum, Diplodia natalensis, Gaeumannomyces graminis, Gibberellafujikuroi, Hormodendron cladosporioides, Lentinus degener* or *tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium roltisi, Stachybotris atra, Stereum, Stilbum* sp., *Trametes trabea, Trichodermapseudokoningi, Trichothecium roseum.*

Fungi of the genus *Colletotrichum* are considered major plant pathogens worldwide. *Colletotrichum* species are responsible for anthracnose of strawberry, cereals, grasses, citrus, and cucurbits; ripe rot of tomato, eggplant, pepper, apple, pear and peach. Anthracnose diseases of strawberry are especially serious problems for fruit and plant production in many areas of the world. Failure to control anthracnose diseases can result in serious economic losses to both U.S. and worldwide agriculture.

*Botrytis* diseases are probably the most common and widely distributed diseases of greenhouse crops, vegetables, ornamentals, and fruits throughout the world. *Botrytis* fruit rot is one of the most destructive diseases of strawberry worldwide. *Botrytis cinerea*, the fungus causing this fruit rot, also incites blossom blight and can infect strawberry leaves and petioles. Fungicide sprays are the main control measure for *Botrytis* fruit rot. Benzimidazole and dicarboximide fungicides have been effective control agents, but in many areas *B. cinerea* has developed chemical resistance.

*Fusarium* vascular wilt of numerous plants is a highly destructive, economically limiting and among one of the most difficult disease to control. Important crops such as most vegetables and flowers, cotton, tobacco, plantation crops, and ornamentals appear to be especially susceptible to certain *Fusarium* species. *Fusarium* toxins present serious post-harvest problems to human health and farm animals on molded corn and in silage. Many *Fusarium* spp. have developed resistance to the benzimidazole class of fungicides.

*Phomopis* leaf and stem blight occurs worldwide. The pathogen, *Phomopis obscurans* causes *Phomopsis* leaf and stem blight and also causes a fruit rot is of strawberry. Other *Phomopsis* species can cause serious leaf and stem blights, dieback of blueberry and rhododendron, *Phomopsis* canker and fruit rot of almond, blight of pistachio, necrosis of many other fruits, trees, and ornamental plants.

*Phomopsis* leaf and cane spot and fruit rot disease of table and wine grapes, caused by the fungus, *Phomopsis viticola*, overwinters in the grape canes producing fruiting bodies. Spores infect new leaves in the spring during rainy weather. The leaf symptoms appear in early to mid-June as small angular dead spots. The lower leaves are the first to show infection. Later in the season, canes, tendrils, leaf petioles and even cluster stems may show elongated, brownish or purplish lesions ¼ inch long. If the disease is severe, the fungus enters the grape berries, probably through the pedicel (berry attachment to the cluster stem). Mechanical harvesting will often shake many berries off the vine ahead of the machine, causing considerable crop loss. 'Niagara' grape is very susceptible to this disease and 'Concord' is less susceptible, but where fungicidal control has been lacking, losses can occur.

The compositions of the invention are particularly useful due to their wide spectrum in relation to cereal diseases (oidium, rust, eyespot, leaf blotch, net blotch, septoria spot and fusarioses). They are also of great interest because of their activity on grey mold (*Botrytis*) and leaf spot, and as a result, they can be applied to products of crop propagation as varied as vines, market garden crops, arboricultural crops and tropical crops such as groundnuts, banana plants, coffee plants, pecan nuts and the like.

In addition to the applications already described above, the compositions according to the invention further possess an excellent biocidal activity towards numerous other varieties of microorganisms amongst which there may be mentioned, without implying a limitation, fungi such as those of the genera:

*Pullularia*, such as the *P. pullulans* species,
*Chaetonium*, such as the *C. globosum* species,
*Aspergillus*, such as the *Aspergillus niger* species,
*Coniophora*, such as the *C. puteana* species.

Because of their biocidal activity, the compositions of the invention make it possible to effectively combat microorganisms whose proliferation creates numerous problems in the agricultural and industrial sectors. To that effect, they are particularly well suited to the protection of plants or industrial products such as timber, leather, paints, paper, rope, plastics and industrial water systems.

Theses compounds and/or compositions may be employed alone or in the form of mixtures with one another and/or a carrier, and/or with other known compatible active agents, especially plant protection agents, such as other fungicides and bactericides, or insecticides, acaricides, rodenticides, nematocides, herbicides, fertilizers, growth-regulating agents, etc., if desired, or in the form of a particular dosage preparation for specific application made therefrom, such a solutions, emulsions, suspensions, powders, paste, and granules which are thus ready for use.

EXAMPLES

The following examples demonstrate different aspects of the present invention. They are intended to be exemplary of the present invention and not intended to be limited thereof.

Example 1

This example demonstrates a general reaction scheme for compounds of the present invention.

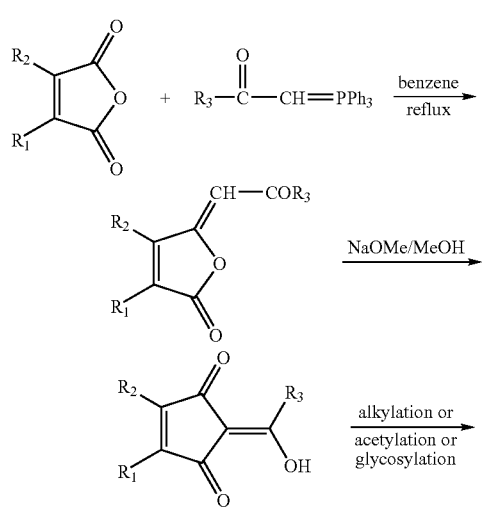

-continued

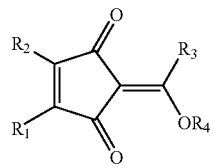

Preparation of the phosphorane

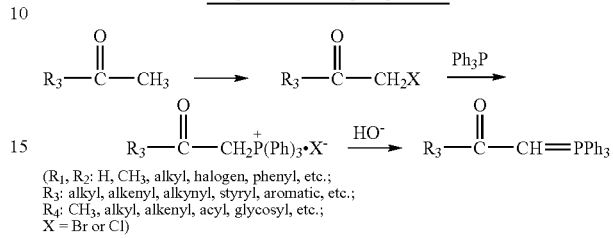

($R_1$, $R_2$: H, $CH_3$, alkyl, halogen, phenyl, etc.;
$R_3$: alkyl, alkenyl, alkynyl, styryl, aromatic, etc.;
$R_4$: $CH_3$, alkyl, alkenyl, acyl, glycosyl, etc.;
X = Br or Cl)

Example 2

This example demonstrates a general reaction scheme for the synthesis of 2-(1-methoxy-ethylidene)-cyclopent-4-ene-1,3-diones.

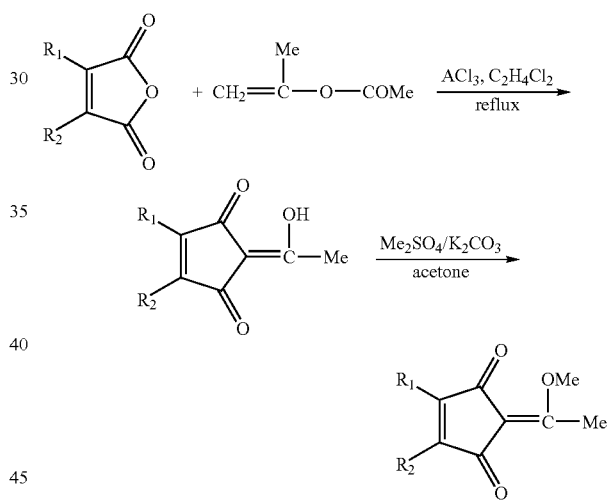

($R_1$, $R_2$: H, alkyl, halogen)

Example 3

This example demonstrates extraction and isolation of compounds of the present invention.

Plant material is collected. The dried root-stem-leave (about 468 g) of *P. coruscans* is ground to a coarse powder and percolated with 95% EtOH. Removal of the solvent under vacuum yields an EtOH extract (about 15.2 g), a portion (about 5 g) of which is directly applied to a silica gel column using a mixture of hexane-$CHCl_3$ as solvents. Two consecutive fractions eluted by hexane-$CHCl_3$ (1:1), which are the most active against *C. albicans* ($IC_{50}$<2 µg/mL), are individually chromatographed on reversed-phase silica gel ($C_{18}$) using 60% $CH_3CN$—$H_2O$ as solvent to afford coruscanones A (Compound 1, about 98 mg) and B (Compound 2, about 135 mg), respectively.

Coruscanone A (Compound 1): yellow powder, mp. 86° C.; UV (MeOH), $?_{max}$ (log e) 232 (4.45), 348 (4.58) nm; IR (NaCl) $\nu_{max}$, 1666, 1615, 1547, 1444, 1306, 1177, 1034, 973, 874, 765, 692 cm$^{-1}$; NMR data, see Tables 1 and 2; HRESIMS m/z [M+H]$^+$ 255.1016 (calcd for $C_{16}H_{15}O_3$, 255.1016), [M+Na]$^+$ 277.0828 (calcd for $C_{16}H_{14}O_3Na$, 277.0835).

Coruscanone B (Compound 2): yellow needles, mp. 124° C.; UV (MeOH), $\lambda_{max}$ (log e) 232 (4.24), 348 (4.40) nm; IR (NaCl) $\nu_{max}$, 1708, 1648, 1630, 1588, 1448, 1353, 1016, 978, 904, 877, 704, 690 cm$^{-1}$; NMR data, see Tables 1 and 2; HRESIMS m/z [M+H]$^+$ 241.0849 (calcd for $C_{15}H_{13}O_3$, 241.0859), [M+Na]$^+$ 263.0660 (calcd for $C_{15}H_{12}O_3Na$, 263.0678).

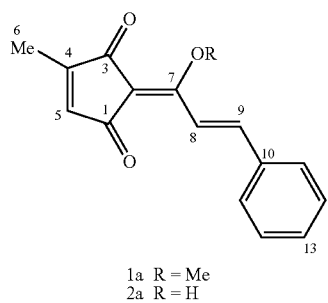

1a R = Me
2a R = H

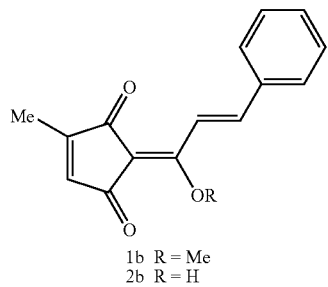

1b R = Me
2b R = H

Example 4

This example shows NMR data of coruscanone A (Compound 1) and B (Compound 2).

TABLE 1

$^{13}$C NMR data for compounds 1 and 2 (d, ppm)

| C | 1a[a] | 1b[a] | 2a[b] | 2b[b] |
|---|---|---|---|---|
| 1 | 191.1 | 193.8 | 191.8 | 200.7 |
| 2 | 109.4 | 109.5 | 103.5 | 103.2 |
| 3 | 195.0 | 192.5 | 201.3 | 192.2 |
| 4 | 156.4 | 156.9 | 154.1 | 158.1 |
| 5 | 140.9 | 140.6 | 140.8 | 137.1 |
| 6 | 10.9 | 11.0 | 10.7 | 11.5 |
| 7 | 168.5 | 168.3 | 167.7 | 167.9 |
| 8 | 121.1 | 121.3 | 117.7 | 117.5 |
| 9 | 142.4 | 142.4 | 143.3 | 143.2 |
| 10 | 136.1 | 136.2 | 134.9 | 134.9 |
| 11 | 128.8 | 128.8 | 128.8 | 128.7 |
| 12 | 129.3 | 129.3 | 129.0 | 129.0 |
| 13 | 130.4 | 130.4 | 130.8 | 130.8 |
| 14 | 129.3 | 129.3 | 129.0 | 129.0 |
| 15 | 128.8 | 128.8 | 128.8 | 128.7 |
| OMe | 64.8 | 64.6 | | |

[a]Measured in $C_6D_6$, 100 MHz.
[b]Measured in CDCl$_3$, 100 MHz.

TABLE 2

$^1$H NMR data for compounds 1 and 2 (d, ppm, J, Hz)

| H | 1a[a] | 1b[a] | 2a[b] | 2b[b] |
|---|---|---|---|---|
| 5 | 6.21 q (1.5) | 6.25 q (1.5) | 6.62 q (1.7) | 6.70 q (1.8) |
| 6 | 1.64 d (1.6) | 1.62 d (1.6) | 2.11 d (1.7) | 2.12 d (1.8) |
| 8 | 8.36 d (15.8) | 8.43 d (15.8) | 7.80 d (16.0) | 7.80 d (16.0) |
| 9 | 7.60 d (15.8) | 7.60 d (15.8) | 7.72 d (16.0) | 7.73 d (16.0) |
| 11 | 7.45 m | 7.45 m | 7.64 m | 7.64 m |
| 12 | 7.02 m | 7.02 m | 7.42 m | 7.42 m |
| 13 | 7.02 m | 7.02 m | 7.42 m | 7.42 m |
| 14 | 7.02 m | 7.02 m | 7.42 m | 7.42 m |
| 15 | 7.45 m | 7.45 m | 7.64 m | 7.64 m |
| OMe | 3.99 s | 3.94 s | | |
| OH | | | 12.11 br s | 12.23 br s |

[a]Measured in $C_6D_6$, 300 MHz.
[b]Measured in CDCl$_3$, 400 MHz.

Example 5

This example shows key HMBC correlations of coruscanone A (1) and B (2).

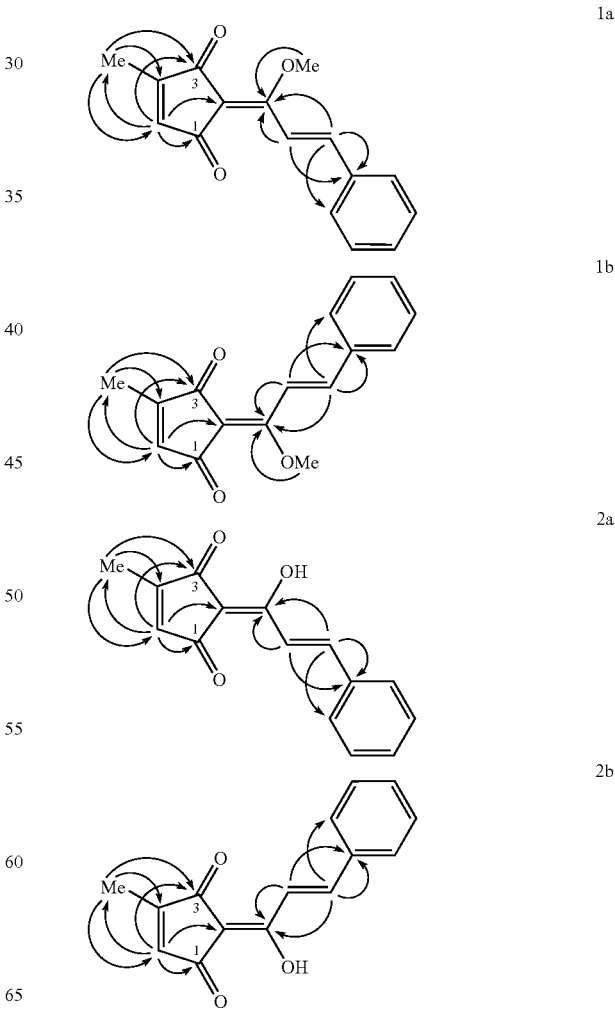

Example 6

This example demonstrates a reaction scheme for producing embodiments of the present invention, coruscanone A (Compound 1) and B (Compound 2).

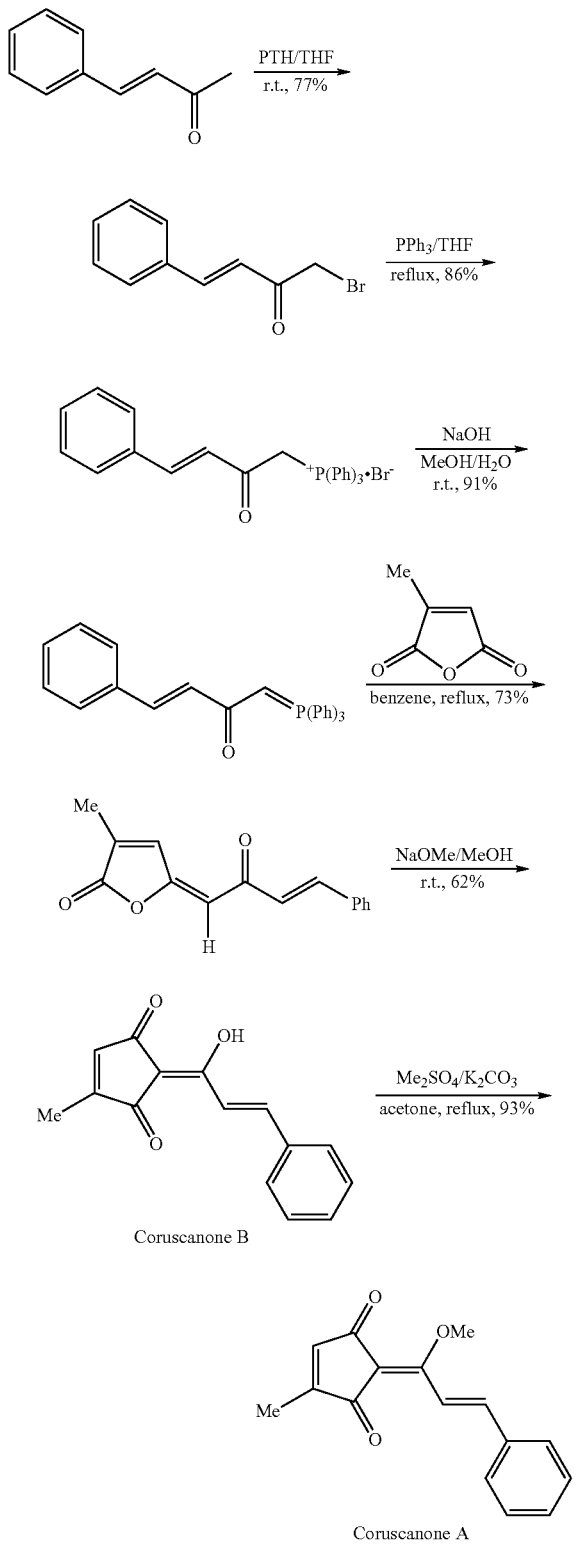

To a solution of styryl methyl ketone (5.0 g, 34.2 mmol) in dry THF (80 mL) at room temperature under nitrogen is slowly added a solution of pyrrolidone hydrotribromide (20.3 g, 40.9 mmol) in dry THF (120 mL) in 1 hr. The mixture is continued to stir at room temperature for 24 hrs. Excess pyrrolidone hydrotribromide is removed by filtration. The filtrate is concentrated to dryness. The resulting residue is dissolved in $Et_2O$, washed with brine and dried ($Na_2SO_4$). Removal of the solvents affords a crude product, which is chromatographed on silica gel eluting with $Et_2O$-hexanes (1:6) to give bromomethyl styryl ketone (5.91 g, 77%) as colorless crystals (from $Et_2O$), $^1H$ NMR (400 MHz, $CDCl_3$) d 7.70 (1H, d, J=16.0 Hz, β-CH=), 7.58 (2H, m, Ph), 7.43 (3H, m, Ph), 6.95 (1H, d, J=16.0 Hz, a-CH=), 4.11 (2H, s, $CH_2Br$); $^{13}C$ NMR (100 MHz, $CDCl_3$) d 191.1 (s, C=O), 145.4 (d, β-CH=), 134.0 (s, Ph), 131.2 (d, Ph), 129.1 (2C, d, Ph), 128.7 (2C, d, Ph), 122.3 (d, a-CH=), 33.3 (t, $CH_2Br$).

To a refluxed solution of triphenylphosphine (5.84 g, 22.3 mmol) in dry THF (25 mL) under nitrogen is slowly added bromomethyl styryl ketone (5.0 g, 22.3 mmol, in 25 ml THF). The reaction mixture is refluxed for 2 hrs. After cooling, the white precipitate is collected by filtration and washed with $Et_2O$. Crystallization of the product with methanol gives triphenyl cinnamoylmethyl phosphonium bromide (9.3 g, 86%) as colorless needles, $^1H$ NMR (400 MHz, DMSO-$d_6$) d 8.02 (1H, d, J=16.0 Hz, β-CH=), 7.87, 7.76, 7.49 (20H, m, Ph), 7.00 (1H, d, J=16.0 Hz, a-CH=), 6.07 (2H, d, J=13.2 Hz $CH_2Br$).

To a suspension of the above phosphonium salts (8.1 g, 16.7 mmol) in water (100 mL) and methanol (100 mL) is added a solution of sodium hydroxide (1.3 g) in water (15 mL) is added. The mixture is stirred at room temperature overnight. After evaporation of methanol, the suspension is extracted with chloroform. The organic layer is washed with brine, dried ($Na_2SO_4$), and concentrated to dryness. Crystallization of the residue with $Et_2O$ gine corresponding phosphorane 4 (6.2 g, 91%) as yellow crystals, $^1H$ NMR (400 MHz, $CDCl_3$) d 7.53, 7.47, 7.31, 7.24 (21H, m), 6.94 (1H, d, J=16.0 Hz, a-CH=), 4.07 (1H, br d, J=21.2 Hz, CH=P); $^{13}C$ NMR (100 MHz, $CDCl_3$) d 182.8 (C=O), 136.8 (d, β-CH=), 133.9, 133.2, 133.1, 132.3, 129.1, 129.0, 128.6, 128.2, 127.5, 127.1, 126.6.

E-4-cinnamoylmethylidene-2-methylbut-2-en-4-olide (5): A solution of 2-methylmaleic anhydride (3) (1.8 g, 16.1 mmol) in benzene (10 mL) is added to a refluxed solution of 4 (5.5 g, 13.5 mmol) in benzene (50 mL) under nitrogen. After refluxing for 6 hrs, TLC indicated complete consumption of 12. The reaction mixture is evaporated to dryness, and the residue is chromatographied on silica gel using hexanes-acetone (4:1) to yield E-4-cinnamoylmethylidene-2-methylbut-2-en-4-olide (5) (2.35 g, 73%) as yellow needles [from chloroform-methanol (1:1)]: mp 160–161 C°, UV (MeOH), $\lambda_{max}$ (log ε) 208 (4.18), 238 (3.98), 334 (4.50) nm; IR (KBr) $\nu_{max}$, 1770, 1678, 1627, 1588, 1451, 1375, 1209, 1098, 1039, 990, 911, 877, 754, 698, 545; $^1$H NMR (400 MHz, CDCl$_3$) δ 8.10 (1H, s, H-3), 7.64 (1H, d, J=16.0 Hz, H-4'), 7.59 (2H, m, H-6',10'), 7.42 (3H, m, H-7',8',9'), 6.88 (1H, d, J=16.0 Hz, H-3'), 6.48 (1H, s, H-1'), 2.11 (3H, s, Me-2); $^{13}$C NMR (100 MHz, CDCl$_3$) δ 188.3 (s, C-2'), 169.2 (s, C-1), 159.2 (s, C-4), 144.0 (d, C-4'), 137.0 (d, C-3), 136.4 (s, C-2), 134.3 (s, C-5'), 131.0 (d, C-8'), 129.1 (2C, d, C-6',10'), 128.6 (2C, d, C-7',9'), 127.5 (d, C-3'), 106.0 (d, C-1'), 11.2 (q, Me-2) (NMR assignments were based on 2D HMBC and NOESY experiments); HRESIMS m/z [M+H]$^+$ 241.0841 (calcd for C$_{15}$H$_{13}$O$_3$, 241.0859), [M+Na]$^+$ 263.0659 (calcd for C$_{15}$H$_{12}$O$_3$Na, 263.0678), [M+K]$^+$ 279.0400 (calcd for C$_{15}$H$_{12}$O$_3$K, 279.0418).

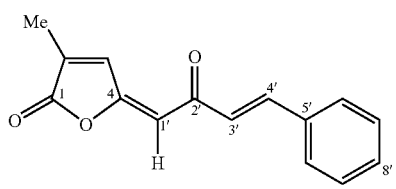

Coruscanone B (Compound 2): A solution of 13 (1.95 g, 8.13 mmol) in dry MeOH (60 mL) is added to a solution of NaOMe (4.41 g, 81.7 mmol) in MeOH (25 mL), and the resulting orange-colored solution is stirred at room temperature for 3 hr and then poured onto ice-water (150 mL) and acidified to pH 1.0 with 2 M HCl. The methanol is removed by evaporation, and the suspension is extracted with Et$_2$O. Evaporation of the dried extracts give the crude product which is purified by crystallization with MeOH to yield coruscanone B (2) as yellow needles (1.21 g, 62%), mp. 125° C.

Note: The NMR spectra indicate this synthetically crystalline compound possesses predominant isomer 2b. Similar to naturally occurring coruscanone B, isomer 2b could rapidly convert to 2a in CDCl$_3$.

Coruscanone A (Compound 1): To a solution of 2 (500 mg) in dry acetone (50 mL) under argon is added K$_2$CO$_3$ (3.0 g). After refluxing for 5 min, Me$_2$SO$_4$ (2.2 mL) is added to the deep yellow-colored solution, and the mixture is continued to reflux for 30 minutes. The K$_2$CO$_3$ is removed by filtration. The filtrate is concentrated to dryness, and the residue is subjected to reversed phase RP-18 column chromatography using aqueous MeOH. The yellow band is eluted by 70% MeOH, and evaporation of the solvent gives coruscanone A (1) (493 mg, 93%) as a yellow powder whose NMR spectra are identical to those of natural one.

Example 7

This example demonstrates a reaction scheme for the synthesis of 2-(1-methoxy-ethylidene)-4-methyl-cyclopent-4-ene-1,3-dione (6).

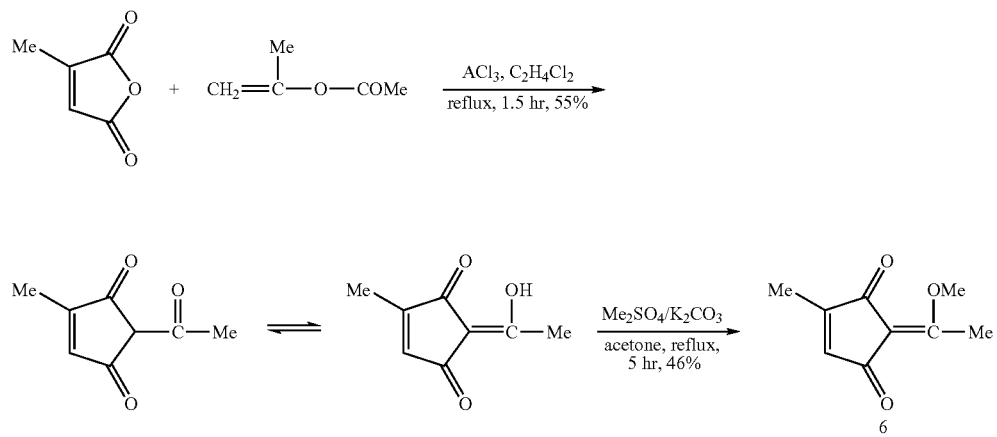

To a solution of 2-methylmaleic anhydride (8.0 g, 71.4 mmol) in dry C$_2$H$_4$Cl$_2$ (200 mL) at room temperature under nitrogen is added anhydrous AlCl$_3$ (32.3 g, 133.4 mmol). The suspension was cooled to 0° C. and α-methylvinyl acetate (10.7 g, 107.1 mmol) was added dropwise in 15 minutes. After finishing the addition, the reaction mixture was heated to reflux for 1.5 hr. After cooling, the reaction mixture was poured into 10% HCl iced water (300 mL). The organic layer was separated. The aqueous layer was extracted with CHCl$_3$ (150 mL×3). The combined organic layers were washed with brine (150 mL) and H$_2$O (200 mL×4) to neutral, dried (Na$_2$SO$_4$), and concentrated to dryness to yield a residue (8.5 g), which was chromatographed on silica gel eluting with hexane-EtOAc (1:2) to afford 2-(1-hydroxy-ethylidene)-4-methyl-cyclopent-4-ene-1,3-dione (5.97 g, 55%) as pale yellow crystals (from Et$_2$O), $^1$H NMR (400 MHz, CDCl$_3$, two isomers) δ 11.8 (br s, OH), 6.50 and 6.42 (br s, H-5), 2.22 (s, vinylic Me), 1.91 (s, Me-4); $^{13}$C NMR (100 MHz, CDCl$_3$, two isomers) δ 200.4, 199.6, 192.1 and 191.7 (1,3-C=O), 176.9 and 176.7 (vinylic C), 157.8 and 153.4 (C-4), 140.5 and 136.2 (C-5), 104.2 and 104.2 (C-2), 17.9 (vinylic Me), 11.2 and 10.2 (Me-4); HRTOFMS m/z [M+H]$^+$ 153.0585 (calcd for C$_8$H$_9$O$_3$, 153.0547).

To a heated solution of the above cyclopentenedione compound (130 mg, 0.855 mmol) and $K_2CO_3$ (0.9 g) in dry acetone (20 mL) was added $Me_2SO_4$ (0.4 mL). After refluxing for 5 hr, the reaction mixture was filtered to remove $K_2CO_3$. The filtrate is concentrated to dryness; and the residue is subjected to reversed phase RP-18 column chromatography using aqueous MeOH. The 80% MeOH eluate was concentrated to dryness; and the residue was chromatographed on silica gel eluting with hexane-EtOAc (5:1 to 2:1) to give 2-(1-methoxy-ethylidene)-4-methyl-cyclopent-4-ene-1,3-dione (6) as two separable isomers in a yellow powder form (32 mg each, 46%). However, the NMR indicated that each of them behaved like coruscanone A, reaching an almost 1:1 equilibrium of two geometric isomers in solution. $^1H$ NMR (400 MHz, $CDCl_3$, one isomer) d 6.52 (br s, H-5), 3.94 (s, OMe), 2.54 (br s, vinylic Me), 1.95 (s, Me-4); $^{13}C$ NMR (100 MHz, $CDCl_3$, one isomer) d 194.5 and 193.0 (1,2-C=O), 173.6 (vinylic C), 155.2 (C-4), 139.7 (C-5), 107.1 (C-2), 55.9 (OMe), 14.0 (vinylic Me), 10.8 (Me-4); HRTOFMS m/z $[M+H]^+$ 167.0682 (calcd for $C_9H_{11}O_3$, 167.0703).

Example 8

This example demonstrates a bioassay method for evaluating in vitro antifungal and antibacterial activity against mammalian cells.

Microorganism Information and Storage. All organisms are obtained from the American Type Culture Collection (Manassas, Va.). They include the fungi *Candida albicans* ATCC 90028, *Candida glabrata* ATCC 90030, *Candida krusei* ATCC 6258, and *Cryptococcus neoformans* ATCC 90113 and the bacterium *Mycobacterium intracellulare* ATCC 23068. Temporary cultures (for immediate use in assays) of all organisms, except *M. intracellulare*, are stored on either agar slants or plates at 4° C. until needed. Long-term storage of strains is accomplished via freezing cells in 10% glycerol/broth at −70° C. [(Sabouraud Dextrose broth (Difco, Detroit) for *Candida* spp. and *C. neoformans*, and Middlebrook 7H9 broth (Difco) with OADC enrichment (BBL, Maryland) for *M. intracellulare*)]. Except for *M. intracellulare*, fresh agar plates are prepared 3–5 days before each assay by streaking agar with suspensions of frozen stocks. *M. intracellulare* slants are prepared from frozen stocks every 4–5 weeks. Fresh slants or plates are prepared by incubating *Candida* spp. on Sabouraud Dextrose agar (Difco) plates for 18–24 h at 37° C., *C. neoformans* on Sabouraud Dextrose agar plates for 72 h at 30° C., and *M. intracelluare* on Lowenstein-Jensen agar slants (BBL) for 1 week at 37° C.

Antimicrobial Assay. Susceptibility testing is performed using a modified version of the National Committee for Clinical Laboratory Standards methods. *M intracelluare* is tested using a modified method of Franzblau, et al. Seventy-two to 96 h prior to the assay, the *M intracellulare* subculture is prepared by resuspending cells from the surface of the slant in Middlebrook 7H9 broth with OADC enrichment and incubating at 37° C. and 10% $CO_2$. On the day of the assay, prepared samples (dissolved in DMSO) are serially-diluted using 20%/0.9% DMSO/saline and transferred in duplicate to 96 well flat bottom microplates. *Candida* spp. and *C. neoformans* inocula are prepared by picking 1–3 colonies from agar plates and resuspending in ~5 mL 0.9% sterile saline. The absorption of 10011 of the saline suspensions and the *M. intracellulare* subculture at 630 nm using the EL-340 Biokinetics Reader (Bio-Tek Instruments, Vermont) is compared either the 0.5 McFarland standard of 0.03 (Mi) or standard curves. The microorganisms are diluted in broth [RPMI 1640/2% dextrose/MOPS at pH 7.3 (Cellgro) for *Candida* spp., Sabouraud Dextrose for *C. neoformans*, and 5% Alamar Blue™(BioSource International, Camarillo, Calif.) in Middlebrook 7H9 broth with OADC enrichment, pH=7.3 for *M. intracellulare* to afford final target inocula of: *Candida* spp.: $1.0 \times 10^4$, *C. neoformans*: $1.0 \times 10^5$, and *M. intracellulare*: $2.0 \times 10^6$ after addition to the samples. The microbial inocula are added to the samples to achieve a final volume of 200 μl. Growth (saline only), solvent and blank (media only) controls are included on each test plate. Drug controls [Ciprofloxacin (ICN Biomedicals, Ohio) for bacteria and Amphotericin B (ICN Biomedicals, Ohio) for fungi] are included in each assay. All organisms are read at either 630 nm using the EL-340 Biokinetics Reader (Bio-Tek Instruments, Vermont) or 544ex/590em, (*M. intracellulare*) using the Polarstar Galaxy Plate Reader (BMG LabTechnologies, Germany) prior to and after incubation: *Candida* spp. at 37° C. for 18–24 h, *C. neoformans* at 30° C. for 72 h, and *M. intracellulare* at 37° C. and 10% $CO_2$ for 72 h. Percent growth is calculated and plotted versus test concentration to afford the $IC_{50}$ (sample concentration that affords 50% growth of the organism) and the minimum inhibitory concentration (MIC) and minimum fungicidal or bactericidal concentrations (MFC/MBCs). The MIC is defined as the lowest test concentration that allows no detectable growth (for *M. intracellulare* no color change from blue to pink). Minimum fungicidal or bactericidal concentrations are determined by removing 5 μl from each clear (or blue) well, transferring to agar and incubating as previously mentioned. The MFC/MBC is defined as the lowest test concentration that kills 100% of the organism (allows no growth on agar).

Example 9

This example demonstrates the antifungal and antibacterial activity of compounds of the present invention. The bioassay method is a modified version of the National Committee for Clinical Laboratory Standards methods, and is same as the one described in example 8 by which the biological data of compounds 1 and 2 (Tables 1 and 2) were obtained, except that the pH of the culture media for *Candida* spp. was changed from 7.3 to 4.5.

TABLE 3

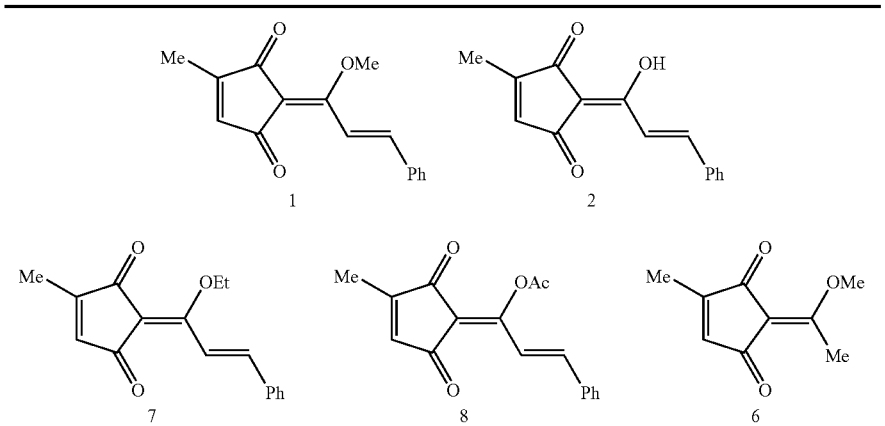

Antimicrobial Activity of Coruscanones A and Its Analogs
(IC$_{50}$[a]/MIC[b]/MFC[c] or MBC[d], μg/mL)

|   | C. albicans ATCC 90028 | C. glabrata ATCC 90030 | C. krusei ATCC 6258 | Cr. neoformans ATCC 90113 | M. intracellulare ATCC 23068 |
|---|---|---|---|---|---|
| 1 | 0.20/0.31/0.63 | 2.50/5.00/na[e] | 2.50/na/na | 1.50/2.50/2.50 | 1.50/2.50/5.00 |
| 2 | 1.00/2.50/5.00 | 1.50/2.50/5.00 | 4.50/na/na | 20.0/na/na | 10.0/20.0/na |
| 7 | 2.00/5.00/10.00 | 4.50/10.00/20.00 | 8.00/na/na | 2.00/20.00/na | 7.50/20.00/20.00 |
| 8 | 1.00/10.00/na | 5.50/na/na | 9.00/na/na | 4.50/na/na | 15.00/20.00/20.00 |
| 6 | 2.00/5.00/20.00 | 3.50/5.00/na | 10.00/na/na | 5.00/na/na | na/na/na |
| AMB[f] | 0.45/1.25/1.25 | 0.20/1.25/1.25 | 0.45/1.25/1.25 | 0.50/1.25/1.25 | nt[g]/nt/nt |
| CIP[h] | nt/nt/nt | nt/nt/nt | nt/nt/nt | nt/nt/nt | 0.30/0.63/1.25 |

[a] 50% inhibitory concentration.
[b] Minimum Inhibitory Concentration.
[c] Minimum Fungicidal Concentration.
[d] Minimum Bactericidal Concentration.
[e] not active.
[f] amphotericin B.
[g] not tested.
[h] ciprofloxacin.

Example 10

This example summarizes agricultural testing and demonstrates agricultural embodiments of the present invention.

Antifungal Methods

Pathogen collection. Isolates of *Colletotrichum acutatum* Simmonds, *Colletotrichum fragariae* Brooks, and *Colletotrichum gloeosporioides* (Penz.) Penz. & Sacc. in Penz. were obtained from B. J. Smith, USDA, ARS, Small Fruit Research Station, Poplarville, Mass. *Colletotrichum fragariae* (isolate CF63), *C. acutatum* (isolate CAGoff), and *C. gloeosporioides* (isolate CG162) were used for all pathogen and bioautography studies. Isolate CF63 is one of the most virulent isolates at infecting strawberry plants and inducing both crown and fruit rot (Smith and Black, 1990). CF63, CAGoff, and CG162 were used as standard test isolates because of our extensive knowledge of these isolates and their known fungicide sensitivity profiles in both bioautography and microtiter formats. The three *Colletotrichum* species were isolated from strawberry (*Fragaria xananassa* Duchesne). *Botrytis cinerea* Pers.:Fr, was isolated from commercial grape (*Vitis vinifera* L.) and *Fusarium oxysporum* Schlechtend:Fr from orchid (*Cynoches* sp.) by David E. Wedge, USDA ARS Natural Products Utilization Research Unit. *Phomopsis viticola* (Sacc.) and *P. obscurans* (Ellis & Everh.) Sutton were from Mike A. Ellis, Ohio State University, Wooster, Ohio. Fungi were grown on potato-dextrose agar (PDA, Difco, Detroit Mich.) in 9 cm petri dishes and incubated in a growth chamber at 24±2° C. and under cool-white fluorescent lights (55±5 mmols·m$^{-2}$·sec$^{-1}$ light) with 12-h photoperiod.

Inoculum preparation. Conidia were harvested from 7–10 day-old cultures by flooding plates with 5 mL of sterile distilled water and dislodging conidia by softly brushing the colonies with an L-shaped glass rod. Conidial suspensions were filtered through sterile miracloth (Calbiochem-Novabiochem Corp., La Jolla Calif.) to remove mycelia. Conidia concentrations were determined photometrically, from a standard curve based on the absorbance at 625 nm and suspensions were then adjusted with sterile distilled water to a concentration of 1.0×10$^6$ conidia/mL.

Bioautography. Extracts containing antifungal compounds were indicated by clear zones of fungal growth inhibition or directly on chromatographic plates using modifications of thin layer chromatography (TLC) bioautographic assays (Homans & Fuchs, 1970; Osborne, et al., 1994; Wedge and Nagle, 2000). Extracts were dissolved. Using a disposable glass micro pipette for each sample, 4 μL of each test extract was placed on the TLC plate and chromatographed in one-dimension.

To detect biological activity directly on the TLC plate, silica gel plates were sprayed with either of the three spore suspensions adjusted to a final concentration of 3.0×10$^5$ conidia/mL with liquid potato-dextrose broth (PDB, Difco, Detroit, Mich.) and 0.1% Tween-80. Using a 50 mL chromatographic sprayer, each glass silica gel thin layer chromatography (TLC) plate with a fluorescent indicator (250 µm, Silica Gel GF Uniplate, Analtech, Inc. Newark Del.) was sprayed lightly (to a damp appearance) three times with the conidial suspension. Inoculated plates were then placed in a 30×13×7.5 cm moisture chamber (398-C, Pioneer Plastics, Inc. Dixon, Ky.) and incubated in a growth chamber at 24±1° C. and 12-h photoperiod under 60±5 mmols·$m^{-2}$·$sec^{-1}$ light. Inhibition of fungal growth was measured 4 d after treatment. Sensitivity of each fungal species to each test compound was determined by comparing size of inhibitory zones.

Microtiter assay. A standardized 96-well microtiter plate assay developed for discovery of natural product fungicidal agents. A 96-well microtiter assay was used to determine sensitivity of *B. cinerea, C. acutatum, C. fragariae, C. gloeosporioides, F. oxysporum, Phomopsis viticola*, and *P. obscurans* to the various antifungal agents in comparison with known fungicidal standards. Vinclozolin, captan, and thiabendazole, which represent three different modes of action, were used as standards in this experiment. Each fungus was challenged in a dose-response format using test compounds where the final treatment concentrations were 0.3, 3.0 and 30.0 µM. Microtiter plates (Nunc MicroWell, untreated; Roskilde, Denmark) were covered with a plastic lid and incubated in a growth chamber at 24±1 C and 12 h photoperiod under 60±5 µmol light. Growth was then evaluated by measuring absorbance of each well at 620 nm using a microplate photometer (Packard Spectra Count, Packard Instrument Co., Downers Grove, Ill.).

Microbioassay Experimental Design. Chemical sensitivity of each fungus 96-well microtiter assay is used to determine sensitivity of *B. cinerea, C. acutatum, C. fragariae, C. gloeosporioides, F. oxysporum, Phomopsis viticola*, and *P. obscurans*. Each chemical is evaluated in duplicate at each dose (0.3, 3.0 and 30.0 µM) and repeated twice in time. Sixteen wells containing broth and inoculum serves as positive controls, eight wells containing solvent at the appropriate concentration and broth without inoculum are used as negative controls. Mean absorbance values and standard errors is used to evaluate fungal growth at 48 hrs and 72 hrs except for *P. obscurans* and *P. viticola* the data are recorded at 120 hrs. Analysis of variance of means for percent inhibition of each fungus at each dose of test compound (n=4) relative to the untreated positive growth controls (n=32) is used to evaluate fungal growth inhibition. Treatments are arranged as a split-plot design replicated twice in time. Whole-plots were fungal isolates and sub-plots are chemicals. Each dose level and response time is analyzed separately. The SAS system's analysis of variance procedure (Statistical Analysis System, Cary, N.C.) is used to identify significant factors and Fisher's protected LSD is used to separate means. The results of these tests are shown below.

Bioassay Methods for Mycotoxin Producing Fungi

Pathogen production. Stock slant isolates of *Aspergillus flavus, Fusarium oxysporum*, and *Fusarium moniliforme* were grown on potato dextrose agar (Difco, Detroit, Mich.) slants for 7 days at room temperature (22° C.).

Inoculum preparation. Prior to a bioassay, 4 ml of 1% potato dextrose broth (PDB, Difco, Detroit, Mich.), pH 4.86, was added to a stock culture slant. The conidia were suspended by gentle agitation using the pipette tip and the population determined with the use of a hemocytometer. The conidia were then diluted to a $10^4$ conidia/ml concentration and incubated for 8 hrs at 22° C. to obtain germinating conidia that were used in the bioassays.

Experimental design of lethality bioassays to determine activity of coruscanone A. Coruscanone A was diluted in 100% methanol with a further dilution in PDB to achieve a stock concentration of 0.032 µg/µl. Test mixtures of germinating conidia and compound 67 were made in sterile 500 µl Eppendorf (Brinkman, Westbury, N.Y.) microcentrifuge tubes. Final test concentrations of compound 67 were 0, 5, 10, 15, 20, 25, and 30 µM in a final volume of 250 µl (0.0635 µg/µl=1.0 µM/250 µl). After an incubation of 30 min, 16 hours and 24 hours at 22° C., aliquots (50 µl) of the each sample were spread on each of 4 PDA plates. The plates were incubated at 22° C. for 2 days and the developed, viable colonies were enumerated. Separate bioassays were also set up at the same time as that with the 30 min incubation period but incubated at 22° C. for 16 and 24 hours, respectively. These samples were spread as previously described and the developing, viable colonies enumerated. Bioassays were performed on three separate occasions per fungus (n=12). Statistical analysis was performed using SigmaPlot 9.0 (p<0.05).

Bioassay Results. Coruscanone A and its structurally related analogs and fractions of plant extract containing these have potential as natural product antifungal and post-harvest anti decay agents that could be applied as a spray, dip or fumigants. Data obtained from in vitro and 96-well microbioassay indicates that coruscanone A is active against fungicide resistant strains of *B. cinerea* inhibitory concentration at 48 h ($IC_{50}$<1.55 µM), *C. gloeosporioides* ($IC_{50}$<3.1 µM), *C. fragariae* ($IC_{50}$<3.1 µM), *C. acutatum* ($IC_{50}$<3.1 µM), and *F. oxysporum* ($IC_{50}$<12.5 µM). Growth inhibition of *Phomopis obscurans* by coruscanone A was greater ($IC_{50}$<3.1 µM) than benomyl ($IC_{50}$<6.25 µM) at 120 hr. Growth inhibition of *Phomopis viticola* by coruscanone A was greater ($IC_{50}$<1.55 µM) than captan ($IC_{50}$<3.1 µM) at 72 hr.

Coruscanone A was not lethal to *Aspergillus flavus* when incubated for only 30 min with the germinating conidia. After 24 hours of incubation, coruscanone was no longer significantly lethal at any of the tested concentrations. *Fusarium oxysporum*. Coruscanone A was not lethal to the germinating conidia of *Fusarium oxysporum* at any of the tested concentrations. However, after the 16 hour incubation period, significant and increasing lethality was observed by coruscanone A for the germinating conidia beginning at a concentration of 15 µM. After the 24 hour incubation period, coruscanone A was significantly and increasingly lethal to the germinating conidia of *Fusarium oxysporum* at and above 10 µM. *Fusarium moniliforme*. Coruscanone A was not significantly lethal to the geminating conidia after a 30 min incubation period. However, after 16 and 24 hours of incubation significant and increasing lethality was observed at and above 5 µM.

TABLE 4

Mean percent fungal growth inhibition of *Botrytis cinerea* in response to three concentrations of coruscanone A and its analogs.

| B. cinerea | 0.3 μm | | 3.0 μm | | 30 μm | |
|---|---|---|---|---|---|---|
| | 48 hrs | 72 hrs | 48 hrs | 72 hrs | 48 hrs | 72 hrs |
| Azoxystrobin | −30.4 ± 40.8 | −67.3 ± 7.6 | −45.8 ± 32.5 | −79.8 ± 3.6 | −58.3 ± 26.5 | −89.1 ± 2.1 |
| Captan | 3.1 ± 26.7 | 3.4 ± 5.8 | −45.9 ± 22.2 | −46.1 ± 5.6 | −76.4 ± 13.4 | −98.7 ± 0.9 |
| Cyprodinil | −96.6 ± 2.3 | 26.56 ± 14.1 | −90.2 ± 3.3 | −81.4 ± 9.2 | −94.2 ± 2.1 | −96.2 ± 1.5 |
| XCL-VI-58A | 2.3 ± 23.9 | 23.0 ± 7.6 | −15.3 ± 19.0 | 15.5 ± 7.5 | −14.3 ± 9.0 | 11.0 ± 4.5 |
| XCL-VI-58C | 15.6 ± 28.7 | 26.5 ± 7.2 | −18.1 ± 21.6 | −1.0 ± 9.0 | 31.6 ± 9.9 | −6.8 ± 4.9 |
| XCL-VI-59D | −6.5 ± 16.0 | 20.7 ± 7.3 | −33.4 ± 12.5 | 7.5 ± 5.6 | −4.5 ± 6.4 | 22.0 ± 6.3 |
| XCL-VI-64A | 12.1 ± 16.9 | 35.2 ± 9.7 | −13.7 ± 14.0 | −3.5 ± 5.2 | −24.9 ± 8.8 | −20.4 ± 4.0 |
| CORUSCANONE A | −7.3 ± 12.8 | 28.1 ± 8.3 | −45.2 ± 16.4 | −15.7 ± 10.6 | −69.6 ± 9.8 | −88.4 ± 5.6 |
| XCL-VI-68A | 26.1 ± 21.1 | 29.2 ± 5.9 | 3.7 ± 8.6 | 39.9 ± 17.2 | 7.2 ± 4.1 | 33.9 ± 5.8 |
| XCL-VI-71C | −24.6 ± 11.6 | 14.3 ± 6.0 | −42.1 ± 5.1 | 4.6 ± 6.3 | −62.6 ± 5.6 | −5.6 ± 10.4 |
| XCL-VI-78E | −13.0 ± 22.9 | 10.5 ± 4.8 | −42.2 ± 6.5 | 6.7 ± 7.0 | −90.2 ± 3.3 | −60.9 ± 2.4 |
| XCL-MAL | −41.5 ± 8.3 | 16.5 ± 11.6 | −28.3 ± 7.4 | 7.9 ± 6.5 | −23.3 ± 13.4 | 3.1 ± 5.6 |
| XCL-VIII-10A | −25.4 ± 11.1 | 1.1 ± 5.4 | −19.8 ± 13.9 | −20.2 ± 5.3 | −66.6 ± 12.2 | −60.9 ± 4.2 |
| XCL-VIII-11B | −25.9 ± 11.2 | 13.2 ± 5.6 | −15.0 ± 20.6 | 14.9 ± 6.2 | −13.6 ± 12.6 | 8.4 ± 5.5 |

TABLE 5

Mean percent fungal growth inhibition of *Colletotrichum acutatum* in response to three concentrations of coruscanone A and its analogs.

| C. acutatum | 0.3 μm | | 3.0 μm | | 30 μm | |
|---|---|---|---|---|---|---|
| | 48 hrs | 72 hrs | 48 hrs | 72 hrs | 48 hrs | 72 hrs |
| Azoxystrobin | −75.1 ± 1.8 | −46.0 ± 1.4 | −89.2 ± 1.8 | −77.4 ± 1.6 | −94.3 ± 1.1 | −84.1 ± 0.8 |
| Captan | 42.5 ± 8.8 | 35.4 ± 6.1 | −98.0 ± 0.9 | −94.1 ± 3.0 | −98.6 ± 0.5 | −99.7 ± 0.2 |
| Cyprodinil | −102.2 ± 0.9 | −94.5 ± 4.4 | −98.1 ± 0.7 | −98.3 ± 0.6 | −99.7 ± 0.7 | −99.0 ± 0.3 |
| XCL-VI-58A | 33.5 ± 5.8 | 29.0 ± 2.9 | −0.2 ± 4.5 | 9.8 ± 4.7 | −56.4 ± 13.8 | −26.6 ± 6.7 |
| XCL-VI-58C | 47.7 ± 4.3 | 36.8 ± 2.0 | 16.4 ± 3.3 | 15.4 ± 2.7 | −37.4 ± 3.9 | −7.3 ± 3.0 |
| XCL-VI-59D | 50.4 ± 9.5 | 42.5 ± 4.8 | 35.3 ± 5.9 | 25.2 ± 4.5 | 26.7 ± 6.6 | 17.4 ± 4.7 |
| XCL-VI-64A | 62.2 ± 5.0 | 50.7 ± 2.0 | 46.6 ± 5.5 | 35.9 ± 3.2 | −6.6 ± 3.6 | −5.8 ± 3.6 |
| CORUSCANONE A | 49.7 ± 6.6 | 38.0 ± 3.0 | −73.1 ± 4.9 | −21.8 ± 4.4 | −95.8 ± 1.9 | −97.6 ± 0.8 |
| XCL-VI-68A | 63.0 ± 7.7 | 54.1 ± 3.4 | 52.3 ± 10.4 | 41.4 ± 7.9 | 38.4 ± 4.6 | 29.1 ± 1.9 |
| XCL-VI-71C | 33.4 ± 5.8 | 36.6 ± 5.2 | 14.6 ± 2.8 | 27.4 ± 6.5 | −26.0 ± 6.5 | −26.0 ± 2.3 |
| XCL-VI-78E | 33.3 ± 5.6 | 34.6 ± 3.7 | 3.0 ± 7.1 | 10.8 ± 3.3 | −57.7 ± 7.1 | −57.7 ± 4.6 |
| XCL-MAL | 54.0 ± 7.1 | 48.9 ± 7.1 | 26.7 ± 6.2 | 29.9 ± 4.4 | 4.6 ± 4.9 | 4.6 ± 4.1 |
| XCL-VIII-10A | 42.1 ± 7.7 | 37.6 ± 6.0 | 7.6 ± 8.3 | 20.9 ± 1.9 | −83.0 ± 3.8 | −83.0 ± 4.9 |
| XCL-VIII-11B | 36.3 ± 7.5 | 38.4 ± 6.0 | 27.3 ± 3.6 | 26.3 ± 3.4 | 7.0 ± 2.8 | 7.0 ± 2.8 |

TABLE 6

Mean percent fungal growth inhibition of *Colletotrichum fragariae* in response to three concentrations of coruscanone A and its analogs.

| C. fragariae | 0.3 μm | | 3.0 μm | | 30 μm | |
|---|---|---|---|---|---|---|
| | 48 hrs | 72 hrs | 48 hrs | 72 hrs | 48 hrs | 72 hrs |
| Azoxystrobin | −68.8 ± 4.0 | −33.5 ± 17.4 | −78.9 ± 4.4 | −80.6 ± 4.8 | −82.0 ± 4.9 | −86.4 ± 4.5 |
| Captan | 18.1 ± 2.7 | −17.5 ± 15.6 | −96.2 ± 1.0 | −74.0 ± 9.3 | −99.7 ± 1.0 | −91.4 ± 5.2 |
| Cyprodinil | −94.1 ± 1.4 | −54.1 ± 19.3 | −89.0 ± 1.6 | −76.7 ± 4.7 | −95.5 ± 0.5 | −92.5 ± 3.2 |
| XCL-VI-58A | −2.6 ± 7.4 | −1.9 ± 4.2 | −13.6 ± 7.1 | −6.5 ± 0.9 | −45.8 ± 7.1 | −31.9 ± 6.1 |
| XCL-VI-58C | 20.5 ± 8.7 | 2.7 ± 4.2 | −7.4 ± 7.7 | −13.1 ± 3.8 | −49.0 ± 7.7 | −39.1 ± 6.7 |
| XCL-VI-59D | −2.5 ± 5.5 | −1.6 ± 3.5 | −4.2 ± 3.9 | −15.0 ± 2.6 | −2.0 ± 3.8 | −12.4 ± 2.6 |
| XCL-VI-64A | 0.4 ± 8.5 | 3.7 ± 5.1 | 1.1 ± 6.0 | −8.3 ± 4.2 | −16.7 ± 6.0 | −31.0 ± 2.3 |
| CORUSCANONE A | −14.1 ± 10.8 | −4.8 ± 5.0 | −94.0 ± 1.9 | −54.6 ± 18.7 | −96.9 ± 1.9 | −67.4 ± 18.3 |
| XCL-VI-68A | −5.6 ± 6.7 | −25.8 ± 12.2 | −21.4 ± 7.9 | −34.3 ± 12.3 | −17.7 ± 7.9 | −32.7 ± 13.9 |
| XCL-VI-71C | −2.2 ± 3.5 | 1.4 ± 3.7 | −0.9 ± 3.6 | −3.8 ± 2.2 | −24.7 ± 10.1 | −9.1 ± 2.2 |
| XCL-VI-78E | −5.7 ± 3.4 | 1.6 ± 7.1 | −37.7 ± 9.8 | −11.4 ± 5.4 | −94.2 ± 2.3 | −51.6 ± 5.4 |
| XCL-MAL | 2.2 ± 4.5 | −3.5 ± 3.3 | −5.1 ± 4.8 | −2.5 ± 2.4 | −14.5 ± 3.2 | −10.0 ± 2.4 |
| XCL-VIII-10A | 15.3 ± 5.1 | 1.2 ± 3.3 | −9.1 ± 2.9 | −7.6 ± 2.7 | −82.3 ± 3.8 | −40.2 ± 2.7 |
| XCL-VIII-11B | 9.5 ± 7.2 | −2.1 ± 4.5 | 6.0 ± 2.4 | −34.0 ± 17.7 | −16.5 ± 7.7 | −41.4 ± 17.7 |

TABLE 7

Mean percent fungal growth inhibition of *Colletotrichum gloeosporoides* in response to three concentrations of coruscanone A and its analogs.

| | 0.3 μm | | 3.0 μm | | 30 μm | |
|---|---|---|---|---|---|---|
| C. gloeosporioides | 48 hrs | 72 hrs | 48 hrs | 72 hrs | 48 hrs | 72 hrs |
| Azoxystrobin | −91.2 ± 2.1 | −71.0 ± 1.4 | −96.3 ± 0.9 | −87.6 ± 2.0 | −97.7 ± 0.5 | −89.8 ± 1.1 |
| Captan | 31.5 ± 7.3 | 38.6 ± 4.5 | −97.3 ± 1.5 | −95.2 ± 1.9 | −98.4 ± 0.5 | −98.6 ± 1.7 |
| Cyprodinil | −89.9 ± 2.7 | −62.9 ± 9.3 | −85.4 ± 6.6 | −76.4 ± 6.3 | −95.1 ± 1.0 | −91.1 ± 1.6 |
| XCL-VI-58A | 30.4 ± 4.9 | 31.7 ± 5.9 | −2.3 ± 8.6 | 18.5 ± 7.2 | −62.5 ± 4.9 | −14.5 ± 4.7 |
| XCL-VI-58C | 39.8 ± 8.4 | 38.8 ± 4.6 | 19.3 ± 4.7 | 32.4 ± 3.1 | −66.1 ± 6.4 | −13.2 ± 3.5 |
| XCL-VI-59D | 45.3 ± 11.7 | 45.5 ± 7.3 | 18.2 ± 5.7 | 19.5 ± 3.5 | 25.0 ± 3.2 | 13.1 ± 3.5 |
| XCL-VI-64A | 46.5 ± 9.9 | 41.6 ± 3.9 | 27.9 ± 5.3 | 29.2 ± 2.2 | −23.9 ± 4.2 | −11.5 ± 2.5 |
| CORUSCANONE A | 37.7 ± 9.0 | 46.7 ± 3.9 | −79.9 ± 2.8 | −13.8 ± 3.7 | −95.2 ± 2.2 | −94.4 ± 1.6 |
| XCL-VI-68A | 36.9 ± 13.7 | 35.7 ± 5.8 | 33.7 ± 6.3 | 33.8 ± 3.2 | 31.4 ± 8.1 | 33.6 ± 2.4 |
| XCL-VI-71C | 30.8 ± 2.9 | 27.6 ± 4.2 | 26.0 ± 5.0 | 22.9 ± 2.6 | −8.0 ± 9.9 | 12.8 ± 2.6 |
| XCL-VI-78E | 22.3 ± 8.1 | 20.8 ± 4.3 | 5.2 ± 4.8 | 13.2 ± 6.4 | −98.0 ± 1.4 | −63.4 ± 6.4 |
| XCL--MAL | 21.4 ± 1.6 | 22.0 ± 4.3 | 14.5 ± 7.3 | 8.2 ± 4.0 | 12.5 ± 1.9 | 17.8 ± 4.0 |
| XCL-VIII-10A | 40.9 ± 4.6 | 37.3 ± 6.2 | −59.1 ± 9.0 | −18.1 ± 3.3 | −99.3 ± 0.4 | −87.6 ± 3.3 |
| XCL-VIII-11B | 34.0 ± 5.3 | 32.4 ± 3.9 | 18.3 ± 4.3 | 17.1 ± 7.3 | −3.4 ± 5.2 | −7.1 ± 7.3 |

TABLE 8

Mean percent fungal growth inhibition of *Fusarium oxysporum* in response to three concentrations of coruscanone A and its analogs.

| | 0.3 μm | | 3.0 μm | | 30 μm | |
|---|---|---|---|---|---|---|
| F. oxysporum | 48 hrs | 72 hrs | 48 hrs | 72 hrs | 48 hrs | 72 hrs |
| Azoxystrobin | −13.0 ± 6.0 | 3.8 ± 3.6 | −66.4 ± 1.4 | −40.1 ± 3.5 | −87.3 ± 0.6 | −64.6 ± 0.8 |
| Captan | 13.6 ± 3.5 | 12.0 ± 2.2 | −50.0 ± 2.8 | −5.4 ± 4.4 | −99.4 ± 0.3 | −99.5 ± 0.4 |
| Cyprodinil | 16.4 ± 3.9 | 7.9 ± 2.9 | 2.6 ± 2.6 | 1.8 ± 2.7 | −67.4 ± 4.3 | −41.5 ± 5.1 |
| XCL-VI-58A | 13.4 ± 5.6 | 9.0 ± 2.8 | −6.7 ± 3.9 | 4.7 ± 4.4 | −26.9 ± 3.2 | −4.4 ± 3.5 |
| XCL-VI-58C | 5.9 ± 4.1 | 5.9 ± 2.4 | −8.9 ± 1.8 | 6.8 ± 2.6 | −33.4 ± 4.2 | −0.9 ± 4.8 |
| XCL-VI-59D | 4.7 ± 6.2 | 4.1 ± 2.9 | −8.1 ± 1.6 | −1.8 ± 1.7 | −6.5 ± 2.4 | −1.0 ± 0.7 |
| XCL-VI-64A | 12.1 ± 5.1 | 7.9 ± 1.4 | −8.3 ± 1.1 | 1.7 ± 2.1 | −33.1 ± 1.2 | −20.8 ± 3.1 |
| CORUSCANONE A | 2.4 ± 4.7 | 12.2 ± 2.1 | −76.9 ± 1.6 | −24.2 ± 3.3 | −99.3 ± 0.2 | −98.9 ± 0.2 |
| XCL-VI-68A | 12.3 ± 4.2 | 8.0 ± 2.0 | 5.1 ± 2.2 | 9.1 ± 2.2 | 9.0 ± 2.0 | 11.3 ± 2.1 |
| XCL-VI-71C | 16.2 ± 3.5 | 10.5 ± 1.7 | −3.0 ± 2.4 | 7.1 ± 2.6 | −92.3 ± 2.1 | −38.7 ± 7.0 |
| XCL-VI-78E | 12.0 ± 4.7 | 9.6 ± 1.8 | −6.7 ± 3.8 | 6.6 ± 4.2 | −94.6 ± 1.4 | −58.4 ± 7.2 |
| XCL-MAL | 13.5 ± 4.6 | 10.6 ± 3.1 | −1.1 ± 2.4 | 6.7 ± 3.8 | −16.1 ± 3.5 | 2.2 ± 3.5 |
| XCL-VIII-10A | 8.2 ± 4.2 | 9.8 ± 2.6 | −19.6 ± 4.0 | 3.4 ± 5.1 | −70.7 ± 3.7 | −29.7 ± 4.9 |
| XCL-VIII-11B | 9.8 ± 4.5 | 8.6 ± 2.7 | −5.2 ± 1.8 | 4.6 ± 2.9 | −25.4 ± 3.4 | −7.7 ± 4.1 |

TABLE 9

Mean percent fungal growth inhibition of *Phomopsis obsucrans* in response to three concentrations of coruscanone A and its analogs.

| | 0.3 μm | | 3.0 μm | | 30 μm | |
|---|---|---|---|---|---|---|
| P. obscurans | 120 hrs | 144 hrs | 120 hrs | 144 hrs | 120 hrs | 144 hrs |
| Azoxystrobin | −73.2 ± 6.7 | −70.2 ± 7.0 | −90.9 ± 6.5 | −87.5 ± 5.3 | −99.3 ± 0.5 | −98.2 ± 0.6 |
| Captan | −37.3 ± 6.6 | −30.9 ± 6.3 | −96.0 ± 1.8 | −98.3 ± 0.6 | −100 ± 0.0 | −99.6 ± 0.2 |
| Cyprodinil | −51.4 ± 5.9 | −46.3 ± 6.0 | −64.5 ± 10.7 | −72.6 ± 3.9 | −86.8 ± 1.3 | −81.5 ± 2.5 |
| XCL-VI-58A | −6.5 ± 11.1 | −5.0 ± 7.9 | −27.0 ± 11.0 | −15.1 ± 10.4 | −72.0 ± 6.6 | −77.1 ± 6.0 |
| XCL-VI-58C | −5.3 ± 11.3 | 4.0 ± 8.8 | −41.9 ± 4.2 | −32.0 ± 3.0 | −88.8 ± 2.9 | −93.3 ± 2.6 |
| XCL-VI-59D | 16.8 ± 20.4 | 22.2 ± 17.5 | −35.7 ± 8.6 | −8.3 ± 15.1 | −47.7 ± 13.1 | −55.2 ± 8.9 |
| XCL-VI-64A | 5.0 ± 15.9 | 21.6 ± 30.5 | −12.1 ± 14.6 | −1.0 ± 19.7 | −76.7 ± 4.9 | −90.9 ± 3.6 |
| CORUSCANONE A | 3.3 ± 19.9 | 33.3 ± 41.6 | −37.4 ± 25.0 | −13.3 ± 36.0 | −88.5 ± 3.4 | −96.9 ± 1.2 |
| XCL-VI-68A | 11.9 ± 11.8 | 13.6 ± 12.7 | 1.8 ± 11.7 | 5.3 ± 9.2 | −31.6 ± 13.2 | −20.3 ± 12.4 |
| XCL-VI-71C | −14.4 ± 8.2 | −0.5 ± 12.5 | −16.8 ± 26.5 | 1.1 ± 29.0 | −85.2 ± 3.6 | −79.3 ± 4.6 |
| XCL-VI-78E | −13.0 ± 6.1 | 0.2 ± 5.4 | 30.0 ± 39.3 | 41.6 ± 38.3 | −86.1 ± 4.6 | −96.3 ± 2.9 |
| XCL-MAL | 50.7 ± 56.5 | 54.7 ± 48.0 | 98.5 ± 101.5 | 60.8 ± 58 | −56.9 ± 9.4 | −64.7 ± 4.6 |
| XCL-VIII-10A | 7.3 ± 14.4 | 11.9 ± 11.3 | −38.9 ± 9.0 | −28.8 ± 9.3 | −78.6 ± 7.2 | −93.1 ± 3.2 |
| XCL-VIII-11B | −2.4 ± 12.8 | 6.6 ± 14.3 | 86.8 ± 74.5 | 71.8 ± 40.8 | −58.1 ± 6.0 | −63.7 ± 2.7 |

TABLE 10

Mean percent fungal growth inhibition of *Phomopsis viticola* in response to three concentrations of coruscanone A and its analogs.

| P. viticola | 0.3 μm | | 3.0 μm | | 30 μm | |
|---|---|---|---|---|---|---|
| | 120 hrs | 144 hrs | 120 hrs | 144 hrs | 120 hrs | 144 hrs |
| Azoxystrobin | −29.5 ± 45.0 | −73.4 ± 16.0 | −124.5 ± 33.0 | −83.2.5 ± 16.7 | −154.1 ± 39.4 | −97.9 ± 1.3 |
| Captan | −118.5 ± 198.7 | 585.2 ± 259.8 | −99.8 ± 38.2 | −95.7 ± 26.0 | −100.0 ± 0.0 | −67.8 ± 21.5 |
| Cyprodinil | −219 ± 122.1 | −1364.3 ± 1122.2 | −184.6 ± 87.0 | 451.7 ± 331.5 | −176.2 ± 48.2 | 80.4 ± 111.6 |
| XCL-VI-58A | −18.6 ± 61.9 | 78.7 ± 46.6 | −66.0 ± 211.3 | −403.3 ± 143.2 | −102.5 ± 117.3 | 96.9 ± 49.2 |
| XCL-VI-58C | 72.6 ± 401 | 1284.4 ± 561.5 | −69.2 ± 178.5 | 308.3 ± 90.2 | −64.9 ± 82.9 | −5.1 ± 35.5 |
| XCL-VI-59D | 22.7 ± 57.7 | −28.1 ± 15.3 | −59.7 ± 95.2 | −28.3 ± 29.2 | −36.4 ± 36.1 | −86.9 ± 7.8 |
| XCL-VI-64A | −77.1 ± 66.0 | −7.0 ± 21.1 | −96.6 ± 60.7 | −69.3 ± 15.4 | −185.8 ± 62.6 | −62.3 ± 19.9 |
| CORUSCANONE A | 7.4 ± 124.1 | 423.2 ± 185.3 | −71.1 ± 50.9 | −71.3 ± 15.7 | −61.8 ± 86.8 | −79.1 ± 13.3 |
| XCL-VI-68A | 17.3 ± 67.8 | 210.1 ± 100.3 | −59.3 ± 106.8 | 174.7 ± 72.9 | −111.8 ± 84.4 | 51.8 ± 47.7 |
| XCL-VI-71C | 38.7 ± 29.2 | −138.3 ± 100.0 | −147.1 ± 129.3 | 210.6 ± 169.5 | −106.9 ± 47.1 | 94.3 ± 107.3 |
| XCL-VI-78E | 28.8 ± 29.9 | 241.9 ± 252.5 | −103.4 ± 114.9 | 417.8 ± 267.1 | −9.6 ± 60.7 | −79.6 ± 13.0 |
| XCL-MAL | 65.2 ± 29.8 | 60.7 ± 78.5 | −90.7 ± 117.3 | 719.1 ± 438.0 | −68.1 ± 162.0 | −1570.1 ± 969.6 |
| XCL-VIII-10A | 47.3 ± 65.2 | 18.3 ± 84.0 | −184.6 ± 87.4 | 171.3 ± 180.8 | −239.9 ± 101.2 | −276.8 ± 112.7 |
| XCL-VIII-11B | −14.0 ± 29.9 | 412.2 ± 331.9 | −86.6 ± 57.7 | 90.5 ± 175.4 | −113.8 ± 77.7 | −86.3 ± 9.2 |

TABLE 11

Lethality of coruscanone A for the Germinating conidia of *Aspergillus flavus*.

| Coruscanone A Concentration (μM) | Time of Incubation of Conidia + Compound (hrs) | Percent of Control Mean | S.E.M. Percent of Control Mean |
|---|---|---|---|
| 0 | 0.5 | 100.0 | 13.8 |
| 5 | 0.5 | 108.6 | 13.1 |
| 10 | 0.5 | 86.6 | 10.7 |
| 15 | 0.5 | 98.0 | 9.8 |
| 20 | 0.5 | 78.9 | 8.6 |
| 25 | 0.5 | 70.0 | 7.4 |
| 30 | 0.5 | 66.5 | 5.1 |
| 0 | 16.0 | 100.0 | 19.9 |
| 5 | 16.0 | 75.2 | 11.4 |
| 10 | 16.0 | 76.4 | 9.3 |
| 15 | 16.0 | 45.4* | 7.9 |
| 20 | 16.0 | 39.1* | 8.9 |
| 25 | 16.0 | 30.5* | 4.1 |
| 30 | 16.0 | 19.5* | 3.9 |
| 0 | 24.0 | 100.0 | 23.0 |
| 5 | 24.0 | 112.8 | 33.2 |
| 10 | 24.0 | 71.8 | 13.4 |
| 15 | 24.0 | 64.8 | 12.0 |
| 20 | 24.0 | 55.7 | 10.1 |
| 25 | 24.0 | 40.6 | 9.0 |
| 30 | 24.0 | 28.7 | 5.8 |

Statistically significant ($p < 0.05$)

TABLE 12

Lethality of coruscanone A for the Germinating Conidia of *Fusarium oxysporum*.

| Coruscanone A Concentration (μM) | Time of Incubation of Conidia + Compound (hrs) | Percent of Control Mean | S.E.M. Percent of Control Mean |
|---|---|---|---|
| 0 | 0.5 | 100.0 | 7.6 |
| 5 | 0.5 | 110.0 | 9.0 |
| 10 | 0.5 | 102.4 | 9.4 |
| 15 | 0.5 | 109.9 | 8.3 |
| 20 | 0.5 | 105.6 | 8.5 |
| 25 | 0.5 | 115.6 | 7.2 |
| 30 | 0.5 | 113.1 | 7.6 |
| 0 | 16.0 | 100.0 | 17.6 |
| 5 | 16.0 | 103.5 | 15.7 |
| 10 | 16.0 | 79.7 | 5.9 |
| 15 | 16.0 | 41.2* | 8.2 |
| 20 | 16.0 | 30.8* | 4.2 |
| 25 | 16.0 | 14.5* | 2.8 |
| 30 | 16.0 | 7.7* | 1.5 |
| 0 | 24.0 | 100.0 | 14.7 |
| 5 | 24.0 | 80.2 | 10.1 |
| 10 | 24.0 | 56.7* | 5.9 |
| 15 | 24.0 | 35.2* | 4.0 |
| 20 | 24.0 | 19.4* | 1.5 |
| 25 | 24.0 | 10.9* | 1.7 |
| 30 | 24.0 | 4.3* | 6.1 |

Statistically significant ($p < 0.05$).

TABLE 13

Lethality of coruscanone A for Germinating Conidia of *Fusarium moniliforme*.

| Coruscanone A Concentration (μM) | Time of Incubation of Conidia + Compound (hrs) | Percent of Control Mean | S.E.M. Percent of Control Mean |
|---|---|---|---|
| 0 | 0.5 | 100.0 | 5.9 |
| 5 | 0.5 | 106.3 | 6.1 |
| 10 | 0.5 | 85.4 | 2.4 |
| 15 | 0.5 | 114.3 | 4.9 |
| 20 | 0.5 | 101.5 | 15.2 |
| 25 | 0.5 | 99.7 | 10.7 |
| 30 | 0.5 | 90.8 | 11.4 |
| 0 | 16.0 | 100.0 | 1.0 |
| 5 | 16.0 | 12.5* | 3.3 |
| 10 | 16.0 | 6.1* | 1.1 |
| 15 | 16.0 | 5.3* | 1.5 |
| 20 | 16.0 | 2.7* | 0.4 |
| 25 | 16.0 | 2.1* | 0.9 |
| 30 | 16.0 | 1.6* | 0.2 |
| 0 | 24.0 | 100.0 | 6.8 |
| 5 | 24.0 | 38.6* | 4.3 |
| 10 | 24.0 | 7.4* | 0.6 |
| 15 | 24.0 | 4.2* | 1.2 |
| 20 | 24.0 | 3.9* | 1.4 |
| 25 | 24.0 | 2.2* | 0.5 |
| 30 | 24.0 | 1.3* | 0.3 |

*Statistically significant ($p < 0.05$)

REFERENCES CITED

The following publications, which primarily present background or supporting information, are incorporated herein by reference in its entirety, and are considered part of this disclosure.

1. Kiang, H. H.; Sim, K. Y. *J. Chem. Soc.* 1962, 4338.
2. Lee, H. H. *Tetrahedron Lett.* 1968, 4243.
3. Liu, S. Y.; Ogihara, Y. *Yakugaku Zasshi* 1975, 95, 114.
4. Leong, Y.-W.; Harrison, L. J.; Bennett, G. J.; Kadir, A. A.; Connolly, J. D. *Phytochemistry* 1998, 47, 891.
5. Aoyama, Y.; Konoike, T.; Kanda, A.; Naya, N.; Nakajima, M. *Bioorg. Med. Chem. Lett.* 2001, 11, 1695.
6. Grohe, K.; Kaspers, H.; Scheinpflug, H. DE 2140737, 1973.
7. Grohe, K.; Frohberger, P. E.; Scheinpflug, H. DE 2248819, 1974.
8. Shigematsu, T.; Tomida, M.; Shibahara, T.; Inoue, K.; Nakazawa, M. JP 51019125, 1976.
9. Inayama, S.; Mamoto, K.; Shibata, T.; Hirose, T. *J. Med. Chem.* 1976, 19, 433.
10. Kawada, H.; Hayashi, S.; Kasugai, A.; Shigematsu, T. JP 52079022, 1977.
11. Simonov, V. V.; Anishchenko, A. F.; Popova, E. N.; Dunaeva, T. P.; Gazizov, R. T.; Simonov, V. D. DE 2804271, 1978.
12. Iwataki, I.; Shibuya, M.; Nakada, A.; Mizuno, M. JP 53101336, 1978.
13. Kobayashi, E.; Koyama, N.; Kato, I. PCT Int. Appl., WO 9904777, 1999.
14. Shestak, P.; Novikov, V. L.; Stekhova, S. I.; Gorshkova, I. A. *Pharm. Chem. J* 1999, 33, 18.
15. Hori, H.; Nagasawa, H.; Ishibashi, M.; Uto, Y.; Hirata, A.; Saijo, K.; Ohkura, K.; Kirk, K. L.; Uehara, Y. *Bioorg. Med. Chem.* 2002, 10, 3257.
16. Watanabe, M.; Hisamatsu, S.; Hotokezaka, H.; Furukawa, S. *Chem. Pharm. Bull.* 1986, 34, 2810.
17. Kalinin, A. V.; Snieckus, V. *Tetrahedron Lett.* 1998, 39, 4999.
18. Bruce, J. M.; Creed, D.; Dawes, K. *J. Chem. Soc. (C)* 1971, 3749.
19. Imgartinger, H.; Stadler, B. *Eur. J. Org. Chem.* 1998, 605.
20. Brehm, I.; Meier, H. *Eur. J. Org. Chem.* 2001, 3307.
21. Brehm, I.; Hinneschiedt, S.; Meier, H. *Eur. J. Org. Chem.* 2002, 3162.
22. Forsén, S.; Merényi, F.; Nilsson, M. *Acta Chem. Scand.* 1964, 18, 1208.
23. Ng, S.; Lee, H.-H.; Bennett, G. J. *Magn. Reson. Chem.* 1990, 28, 337.
24. Ferreira, D.; Roux, D. G. *J. Chem, Soc. Perkin Trans* 11977, 134.
25. Clemo, N. G.; Gedge, D. R.; Pattenden, G. *J. Chem. Soc., Perkin Trans. I* 1981, 1448.
26. Li, X.-C.; ElSohly, H. N.; Nimrod, A. C.; Clark, A. M. *J. Nat. Prod.* 1999, 62, 767.
27. Marr, K. A., Lyons; C. N, Rustad, T; Bowden, R. A, White, T. C. *Antimicrob. Agents Chemother.* 1998, 42, 2584.
28. White T. C. *Antimicrob. Agents Chemother.* 1997, 41, 1482.
29. Pfaller, M. A.; Rhine-Chalberg, J.; Redding, S. W.; Smith, J.; Farinacci, G.; Fothergill, A. W.; Rinaldi, M. G. *J. Clin. Micro.* 1994, 32, 59.
30. Odds, F. C. *Int. J. Std. AIDS* 1992, 3, 157.
31. Coleman, D. C.; Bennett, D. E.; Sullivan, D. J.; Gallagher, P. J.; Henman, M. C.; Shanley, D. B.; Russell, R. J. *Crit. Rev. Microbiol.* 1993, 19, 61.
32. Nilsson, M. *Acta Chem. Scand.* 1964, 18: 441.
33. Novikov, V. L.; Shestak, 0. P.; Kamernitskii, A. V.; Elyakov, G. B. *Izvestiya Akademii Nauk SSR, Seriya Khimicheskaya* 1981, 1, 236.
34. Choi, Y. H.; Kwon, S. Y.; Kim, J. H.; Beak, N. I.; Choi, G. J.; Cho, K. Y.; Lee, B. M. *Han'guk Nonghua Hakhoechi* 2003, 46:151.
35. NCCLS, Reference Method for Broth Dilution Antifungal Susceptibility Testing of Yeasts; Approved Standard M27-A2. National Committee on. Clinical Laboratory Standards, 2002 22 (15).
36. NCCLS, Reference method for broth dilution antifungal susceptibility testing of filamentous fungi; approved standard, M38-A. National Committee on Clinical Laboratory Standards, 2002, 22(16).
37. NCCLS, Methods for Dilution Antimicrobial Susceptibility Tests for Bacteria that Grow Aerobically M7-A5. National Committee on Clinical Laboratory Standards, 2000, 20(2).
38. NCCLS, *Susceptibility Testing of Mycobacteria, Nocardia, and Other Aerobic Actinomycetes; Tentative Standard—Second Edition*, M24-T2. National Committee on Clinical Laboratory Standards, 2000, 20(26).
39. Franzblau, S. G.; Witzig, Richard S.; Mclaughlin, James C.; Torres, Patricia; Madico, Guillermo; Hernandez, Antonio; Degnan, Michelle T.; Cook, Mary B.; Quenzer, Virginia K.; Ferguson, Robert M.; Gilman, Robert H. *J. Clin. Microbiol.* 1998, 36, 362.

The invention thus being described, it will be apparent to those skilled in the art that various modifications and variations can be made in the present invention without departing from the scope or spirit of the invention. All such modifications and variations are considered to be within the scope of the present invention and not a departure therefrom.

Unless otherwise specifically indicated, all numbers expressing quantities of ingredients, properties such as reaction conditions, and so forth used in the Specification and claims are to be understood as being modified in all instances by the term "about." Accordingly, unless indicated to the contrary, the numerical parameters set forth in the Specification and claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications are referenced. All such references, specifically including those cited in the "References Cited" section are incorporated herein by reference.

We claim:
1. A compound of the following formula:

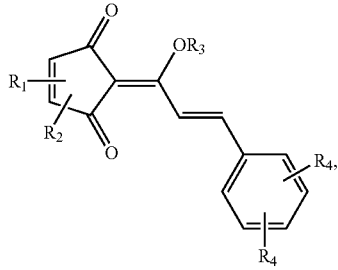

where $R_{1-4}$ are each independently H, alkyl, methyl, acyl, halogen, phenyl; provided that when $R_3$ is methyl and each $R_4$ is H, $R_1$ and $R_2$ are not both H; and provided that when $R_3$ and $R_4$ are both H, $R_1$ and $R_2$ are not both methyl; stereoisomers and pharmaceutically acceptable salts thereof.

2. A compound of claim 1, of the following formula:

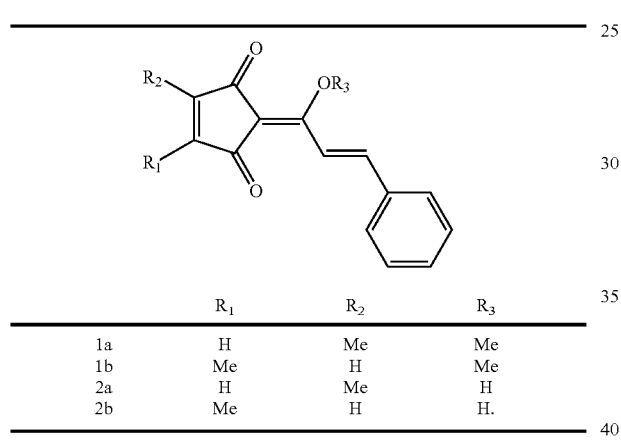

|    | $R_1$ | $R_2$ | $R_3$ |
|----|-------|-------|-------|
| 1a | H     | Me    | Me    |
| 1b | Me    | H     | Me    |
| 2a | H     | Me    | H     |
| 2b | Me    | H     | H.    |

3. A compound of claim 1, of the following formula:

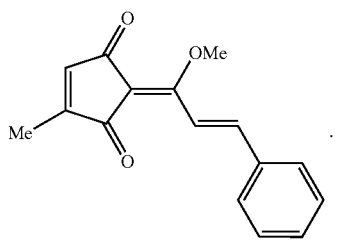

4. A compound of claim 1, of the following formula:

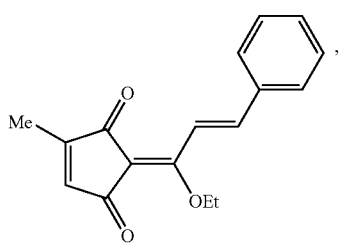

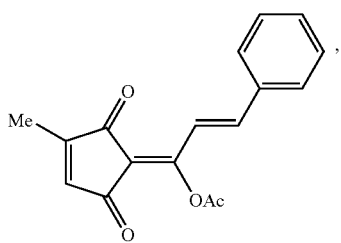

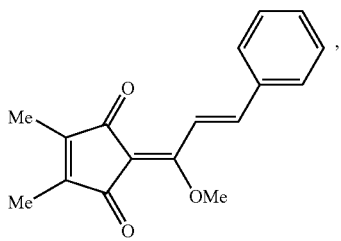

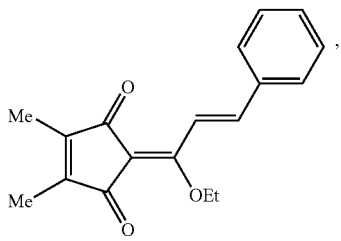

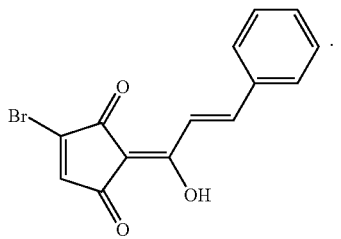

5. A compound of claim 1, of the following formula:

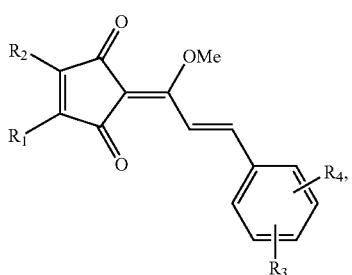

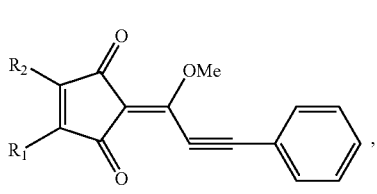

-continued

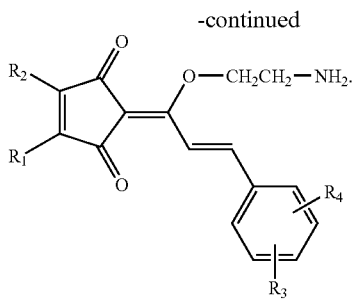

6. A pharmaceutical composition, which comprises a compound of claim 1 and a pharmaceutically acceptable carrier.

7. An agrochemical composition, which comprises a compound of claim 1 and an agriculturally acceptable carrier.

8. A method of treating, preventing, and/or controlling a fungal infection, comprising administering to a patient in need thereof an effective fungal treating amount or an effective fungal preventing amount of a compound of the following formula:

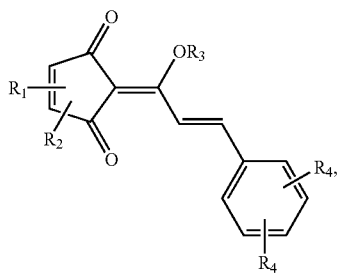

where $R_{1-4}$ are independently H, alkyl, methyl, alkoxy, methoxy, acyl, halogen, phenyl; provided that when $R_1$ is methoxy, $R_2$ is H and $R_4$ is H, then $R_3$ is not methyl;

and a pharmaceutically acceptable carrier.

9. The method of claim 8, wherein the fungi is selected from the group consisting of *Microsporum canis, Ctenomyces mentagrophytes, Trichophyton rubrum, Phialophora verrucosa, Cryptococcus neoformans, Candida tropicalis, Candida albicans, Candida glabrata, Candida krusei, Candida pseudotropicalis, Candida parapsilosis, Aspergillus fumigatus, Aspergillus flavus, Mucor* species, *Sporotricum schenckii* and *Saprolegnia* species.

10. The method of claim 8, wherein the compound is of the following formula:

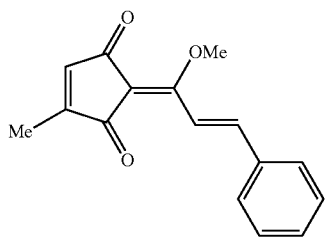

11. The method of claim 8, wherein the compound is of the following formula:

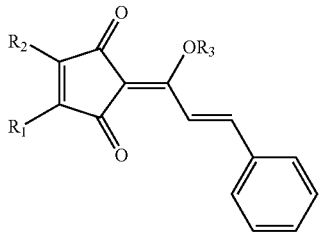

| | $R_1$ | $R_2$ | $R_3$ |
|---|---|---|---|
| 1a | H | Me | Me |
| 1b | Me | H | Me |
| 2a | H | Me | H |
| 2b | Me | H | H. |

12. A method of treating, preventing, and/or controlling fungal activity in plants, comprising administering to the plant or soil an effective fungal treating, preventing, and or controlling amount of a compound of the following formula:

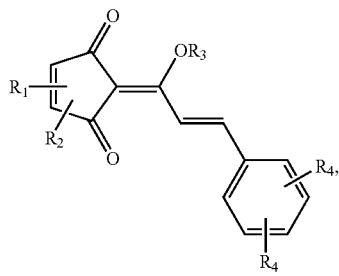

where $R_{1-4}$ are independently H, alkyl, methyl, alkoxy, methoxy, acyl, halogen, phenyl; provided that when $R_1$ is methoxy, $R_2$ is H and $R_4$ is H, then $R_3$ is not methyl;

and stereoisomers thereof, and an agriculturally acceptable carrier.

13. The method of claim 12, wherein the compound is of the following formula:

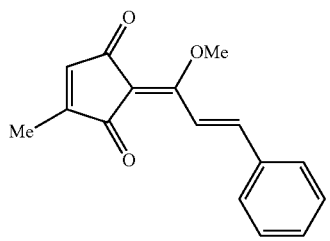

14. A method of treating or preventing a fungal infection, comprising administering to a patient in need thereof an effective fungal treating amount or an effective fungal preventing amount of a compound of the following formula:

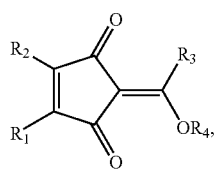

wherein $R_1$ and $R_2$ are independently H, alkyl, halogen, phenyl;

$R_3$ is alkyl, alkenyl, alkynyl, styryl, heterocycle, cycloalkyl, aryl, alkylcycloalkyl, alkylheterocycle, alkylaryl;

$R_4$ is H, alkyl, alkenyl, acyl, glycosyl, phosphate, sulphate;

and stereoisomers, and pharmaceutically acceptable carrier.

15. The method of claim 14, wherein the fungi is selected from the group consisting of *Microsporum canis, Ctenomyces mentagrophytes, Trichophyton rubrum, Phialophora verrucosa, Cryptococcus neoformans, Candida tropicalis, Candida albicans, Candida glabrata, Candida krusei, Candida pseudotropicalis, Candida parapsilosis, Aspergillus fumigatus, Aspergillus flavus, Mucor* species, *Sporotricum schenckii* and *Saprolegnia* species.

16. The method of claim 14, wherein the compound is of the following formula formula:

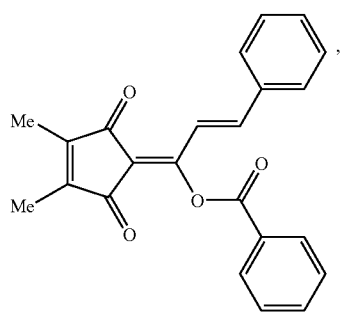

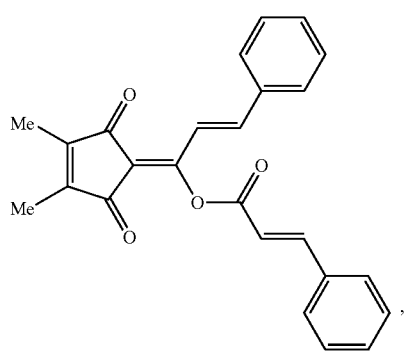

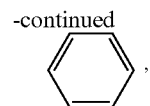

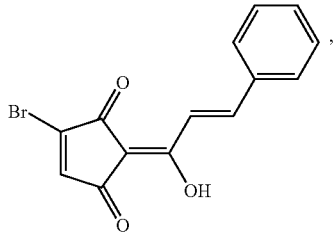

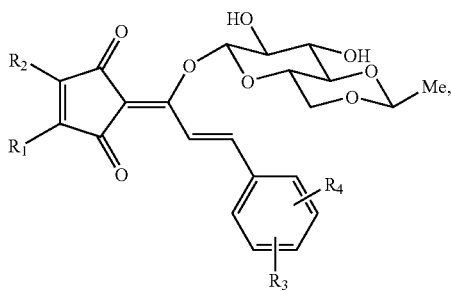

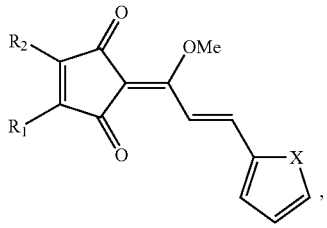

(X = O or S)

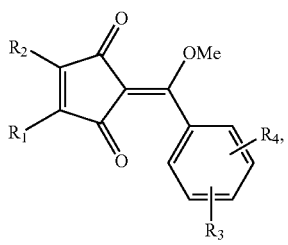

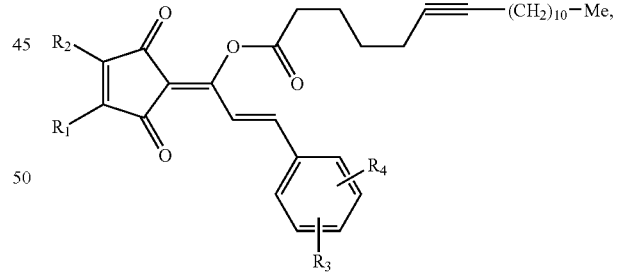

and stereoisomers thereof.

17. The method of claim 14, wherein the compound is of the following formula:

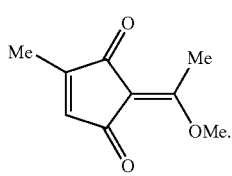

18. A method of treating, preventing, and/or controlling fungal activity in plants, comprising administering to the plant or soil an effective fungal treating, preventing, and/or controlling amount of a compound of the following formula:

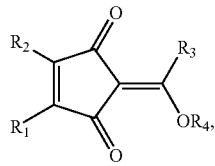

wherein $R_1$ and $R_2$ are independently H, alkyl, halogen, phenyl;

$R_3$ is alkyl, alkenyl, alkynyl, styryl, heterocycle, cycloalkyl, aryl, alkylcycloalkyl, alkylheterocycle, alkylaryl;

$R_4$ is H, alkyl, alkenyl, acyl, glycosyl, phosphate, sulphate;

and stereoisomers, analogs thereof, and an agriculturally acceptable carrier.

19. The method of claim 16, wherein the compound is of the following formula:

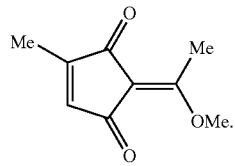

20. A compound of the following formula:

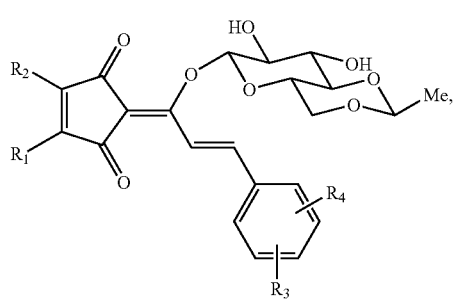

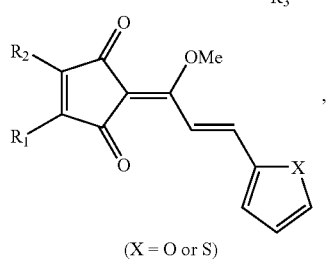

(X = O or S)

-continued

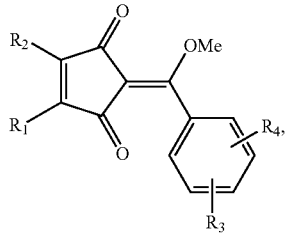

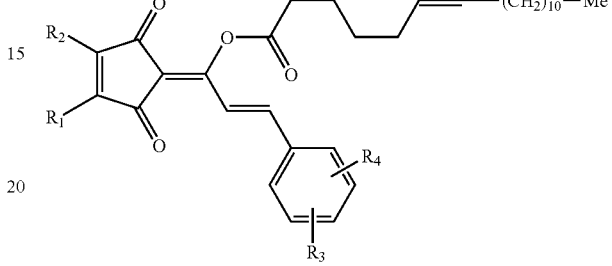

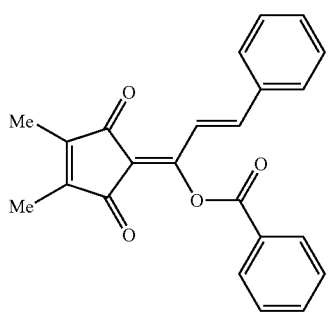

, or

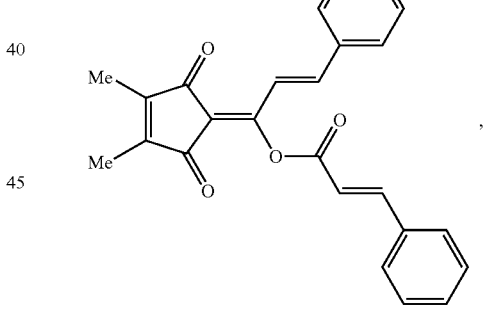

, and stereoisomers and pharmaceutically acceptable salts thereof.

21. A pharmaceutical composition, which comprises a compound of claim 20 and a pharmaceutically acceptable carrier.

22. An agrochemical composition, which comprises a compound of claim 20 and an agriculturally acceptable carrier.

* * * * *